United States Patent
Bouma et al.

(10) Patent No.: US 11,473,897 B2
(45) Date of Patent: Oct. 18, 2022

(54) METHOD AND APPARATUS FOR MEASURING DEPTH-RESOLVED TISSUE BIREFRINGENCE USING SINGLE INPUT STATE POLARIZATION SENSITIVE OPTICAL COHERENCE TOMOGRAPHY

(71) Applicants: The General Hospital Corporation, Boston, MA (US); Nanyang Technological University, Singapore (SG)

(72) Inventors: Brett Bouma, Quincy, MA (US); Martin Villiger, Cambridge, MA (US); Xinyu Liu, Singapore (SG); Linbo Liu, Cambridge, MA (US); Qiaozhou Xiong, Singapore (SG); Nanshuo Wang, Singapore (SG)

(73) Assignees: The General Hospital Corporation, Boston, MA (US); Nanyang Technological University, Singapore (SG)

( * ) Notice: Subject to any disclaimer, the term of this patent is extended or adjusted under 35 U.S.C. 154(b) by 0 days.

(21) Appl. No.: 17/284,641

(22) PCT Filed: Oct. 14, 2019

(86) PCT No.: PCT/US2019/056048
§ 371 (c)(1),
(2) Date: Apr. 12, 2021

(87) PCT Pub. No.: WO2020/077328
PCT Pub. Date: Apr. 16, 2020

(65) Prior Publication Data
US 2021/0396509 A1 Dec. 23, 2021

Related U.S. Application Data

(60) Provisional application No. 62/744,917, filed on Oct. 12, 2018.

(51) Int. Cl.
*G01B 9/02* (2022.01)
*G01B 9/02091* (2022.01)
(Continued)

(52) U.S. Cl.
CPC ......... *G01B 9/02091* (2013.01); *G01N 21/23* (2013.01); *G01B 2290/70* (2013.01); *G01N 33/4833* (2013.01)

(58) Field of Classification Search
CPC ......... G01B 9/02091; G01N 2021/216; G01N 21/23; G01N 21/4795; G01N 33/4833
See application file for complete search history.

(56) References Cited

U.S. PATENT DOCUMENTS 6,961,123 B1  11/2005  Wang
2004/0233457 A1*  11/2004  Podoleanu ............. G01N 21/23
                                                356/479
(Continued)

FOREIGN PATENT DOCUMENTS

WO    2002075242 A2   9/2002
WO    2006050320 A2   5/2006

OTHER PUBLICATIONS

Brinkmeyer, E. "Forward-backward transmission in birefringent single-mode fibers: interpretation of polarization-sensitive measurements." Optics letters 6.11 (1981): 575-577.
(Continued)

*Primary Examiner* — Tarifur R Chowdhury
*Assistant Examiner* — Jonathon Cook
(74) *Attorney, Agent, or Firm* — Quarles & Brady LLP

(57) ABSTRACT

A method for determining a retardance of a layer of a sample. The method includes: transmitting a first portion of a polarized light to a sample arm of an optical system and a second portion of the polarized light to a reference arm of the optical system; combining first return light returned from
(Continued)

the sample arm and second return light from the reference arm; detecting, using a detector, the combined light along a first polarization state and a second polarization state to produce polarization data, the second polarization state being different from the first polarization state; determining, using a processor coupled to the detector, polarization states of light returning from upper and lower surfaces of a layer of the sample based on detecting the combined light; and determining, using the processor, a retardance of the layer of the sample based on the determined polarization states.

26 Claims, 10 Drawing Sheets

(51) Int. Cl.
  *G01N 21/23* (2006.01)
  *G01N 33/483* (2006.01)

(56) References Cited

U.S. PATENT DOCUMENTS

| | | | |
|---|---|---|---|
| 2007/0109554 A1* | 5/2007 | Feldchtein | G01B 9/02057 356/477 |
| 2008/0007734 A1 | 1/2008 | Park | |
| 2008/0291463 A1* | 11/2008 | Milner | G01B 9/02069 356/491 |
| 2010/0182609 A1* | 7/2010 | Wang | G01B 9/02091 356/491 |
| 2017/0349103 A1 | 12/2017 | Tonar | |
| 2018/0014730 A1 | 1/2018 | Lee | |
| 2018/0156596 A1 | 6/2018 | Wang | |

OTHER PUBLICATIONS

Cense, B., et al. In vivo depth-resolved birefringence measurements of the human retinal nerve fiber layer by polarization-sensitive optical coherence tomography. Opt. Lett. 27, 1610-1612 (2002).
Cloude, S. R. et al. Concept of polarization entropy in optical scattering. Opt. Eng. 34, 1599 (1995).
Corsi, F., et al. Polarization mode dispersion characterization of single-mode optical fiber using backscattering technique. J. Light. Technol. 16, 1832-1843 (1998).
De Boer, J. F., et al. Polarization sensitive optical coherence tomography—a review [Invited]. Biomed. Opt. Express 8, 1838 (2017).
Fan, C. et al. Mapping local optical axis in birefringent samples using polarization-sensitive optical coherence tomography. J. Biomed. Opt. 17, 110501 (2012).
Ghosh, N. et al. "Tissue polarimetry: concepts, challenges, applications, and outlook." Journal of biomedical optics 16.11 (2011): 110801.
Gil, J. J. Polarimetric characterization of light and media. Eur. Phys. J. Appl. Phys. 40, 1-47 (2007).
Gordon, J. P., et al. "PMD fundamentals: Polarization mode dispersion in optical fibers." Proceedings of the National Academy of Sciences 97.9 (2000): 4541-4550.
Guo, S., et al. Depth-resolved birefringence and differential optical axis orientationmeasurements with fiber-based polarization-sensitive optical coherence tomography. Opt. Lett. 29, 2025-2027 (2004).
Hee, M. R., et al. Polarization-sensitive low-coherence reflectometer for birefringence characterization and ranging. J. Opt. Soc. Am. B 9, 903 (1992).
Hitzenberger, C., et al. Measurement and imaging of birefringence and optic axis orientation by phase resolved polarization sensitive optical coherence tomography. Opt. Express 9, 780-790 (2001).
International Searching Authority. International Search Report and Written Opinion for application PCT/US2019/056048, dated Jan. 14, 2020. 10 pages.
Liu, X. et al. Tissue-like phantoms for quantitative birefringence imaging. Biomed. Opt. Express 8, 4454-4465 (2017).
Makita, S., et al. Generalized Jones matrix optical coherence tomography: performance and local birefringence imaging. Opt. Express 18, 854-876 (2010).
Mujat, M., et al. Autocalibration of spectral-domain optical coherence tomography spectrometers for in vivo quantitative retinal nerve fiber layer birefringence determination. J. Biomed. Opt. 12, 041205 (2007).
Park, B. H., et al., "Real-time multi-functional optical coherence tomography," Opt. Express 11(7), 782-793 (2003).
Pircher, M., et al. Polarization sensitive optical coherence tomography in the human eye. Prag. Retin. Eye Res. 30, 431-451 (2011).
Potton, R. J. Reciprocity in optics. Reports Prag. Phys. 67, 717-754 (2004).
Qi, J. et al. Mueller polarimetric imaging for surgical and diagnostic applications: a review. J. Biophotonics 10, 950-982 (2017).
Sassen, K. The Polarization Lidar Technique for Cloud Research: A Review and Current Assessment. Bull. Am. Meteorol. Soc. 72, 1848-1866 (1991).
Todorovic, M., et al. Determination of local polarization properties of biological samples in the presence of diattenuation by use of Mueller optical coherence tomography. Opt. Lett. 29, 2402 (2004).
Tuchin, V. V. Polarized light interaction with tissues. J. Biomed. Opt. 21, 071114 (2016).
Tyo, J. S., et al. Review of passive imaging polarimetry for remote sensing applications. Appl. Opt. 45, 5453 (2006).
Van Albada, M. P., et al. "Polarisation effects in weak localisation of light." Journal of Physics D: Applied Physics Oct. 14, 1988, vol. 21 (10S), p. S28-S31. Year: 1988.
Van Deventer, et al. "Polarization properties of Rayleigh backscattering in single-mode fibers." Journal of Lightwave Technology 11.12 (1993): 1895-1899.
Vansteenkiste, N., et al. "Optical reversibility theorems for polarization: application to remote control of polarization." JOSA A 10.10 (1993): 2240-2245.
Villiger, M. et al. Deep tissue volume imaging of birefringence through fibre-optic needle probes for the delineation of breast tumour. Sci. Rep. 6, 28771 (2016).
Villiger, M. et al. Spectral binning for mitigation of polarization mode dispersion artifacts in catheter-based optical frequency domain imaging. Opt. Express 21, 16353-16369 (2013).
Villiger, M., et al. "Polarization-Sensitive Optical Coherence Tomography with a Single Input Polarization State." 2019 IEEE Photonics Conference (IPC). Sep. 29-Oct. 3, 2019. IEEE.
Villiger, M., et al., "Coronary Plaque Microstructure and Composition Modify Optical Polarization," JACC Cardiovasc. Imaging 11(11), 1666-1676 (2018).
Villiger, M., et al., "Optic axis mapping with catheter-based polarization-sensitive optical coherence tomography," Optica 5(10), 1329-1337 (2018).
Wang, N. et al. Polarization management to mitigate misalignment-induced fringe fading in fiber-based optical coherence tomography. Opt. Lett. 42, 2996 (2017).
Xiong, Q., et al. "Polarization constraints in reciprocal unitary backscattering." arXiv preprint arXiv:1903.01142 (2019).
Fanjul-Velez et al., Polarimetry of Birefringent Biological Tissues with Arbitrary Fibril Orientation and Variable Incidence Angle, Optics Letters, 2010, 35(8):1163-1165.
Villiger et al., Reciprocity Constraints in Catheter-Based Polarimetry, In 2016 IEEE Photonics Conference (IPC), 2016, pp. 136-137.
European Patent Office, Extended Search Report, Application No. 19870605.3, dated Jul. 8, 2022, 9 pages.

* cited by examiner

METHOD AND APPARATUS FOR MEASURING DEPTH-RESOLVED TISSUE BIREFRINGENCE USING SINGLE INPUT STATE POLARIZATION SENSITIVE OPTICAL COHERENCE TOMOGRAPHY

CROSS-REFERENCE TO RELATED APPLICATIONS

This application is a U.S. National Stage of International Application No. PCT/US2019/056048 filed Oct. 14, 2019 which is based on, claims priority to, and incorporates herein by reference in its entirety U.S. Provisional Patent Application Ser. No. 62/744,917 filed on Oct. 12, 2018, and entitled "Method and Apparatus for Measuring Depth-Resolved Tissue Birefringence Using Single Input State Polarization Sensitive Optical Coherence Tomography".

BACKGROUND INFORMATION

Near infrared spectral band broadband or wavelength sweeping laser sources are commonly used as the imaging light source in Optical Coherence Tomography ("OCT") systems. The light emitted from the source is divided and directed into different paths, usually called the "reference arm" and the "sample arm," then redirected and combined again resulting in interference via a Michelson or Mach-Zehnder configuration, or similar hybrid forms, which is then further received by detectors or spectrometers and processed by a computer. In the reference arm, a reflector is often used to direct the light back, providing a designated optical path length to the light. In the sample arm, the light is focused into the specimen and backscattered by the structures inside the specimen. The optical path length differences of the light between the reference arm and sample arm are encoded in the recorded interference fringes in the spectral domain. Using an extraction algorithm, typically inverse Fourier transformation, the depth-resolved intensity of the light backscattered from the tissue is extracted to form an image representing the inside structure of the specimen.

There is a need for improved OCT methods which provide additional information such as birefringence information while obtaining data at high imaging speeds.

SUMMARY OF THE INVENTION

Polarization Sensitive Optical Coherence Tomography ("PS-OCT") uses a polarization-sensitive detection scheme to record the polarization state of the output light scattered back from the sample. Therefore, PS-OCT can reveal tissue polarization properties, in addition to the conventional sample reflectivity. Specifically, PS-OCT can detect tissue polarization properties including retardation and diattenuation between the two principal polarization states, including determination of the principal polarization states.

Birefringence describes the difference in the refractive index experienced by light polarized along the fast and slow principal polarization state, or optic axis, respectively, of a birefringent medium. Birefringence results in retardation, i.e. delaying of the light polarized along the slow optic axis direction, resulting in a net retardance, i.e. delay, after propagation along a defined distance. While retardance is usually expressed relative to the wavelength of the employed light, birefringence is an absolute number. Throughout this disclosure, retardation and birefringence may be used interchangeably.

One type of PS-OCT, known as "single input state PS-OCT," uses light with a single, typically circular, illumination polarization state to probe the tissue. Due to the presence of retardation in the sample, the polarization state of the light will change while propagating in the tissue. The depth-resolved polarization states of backscattered light can be extracted from the fringes recorded by the detectors and allow computing the cumulative change in polarization state compared to the input state, i.e. the depth-dependent retardance. Detectors in PS-OCT usually comprise a polarization beam splitter which separates the horizontal and vertical components of the light beam and separately records the interference fringes in each channel.

As the probing light is focused into the tissue structure and scattered back for collection, the direct interpretation of the depth-resolved output polarization states of the light corresponds to the effect of the cumulated polarization properties of the tissue, including the cumulated retardation and optic axis orientation. However, in most cases, the tissue being examined has varying structures and consists of layers with distinct birefringence properties, making it difficult to read the maps of cumulated retardation. On the other hand, a map of local retardation properties of the tissue inherently relates to the birefringence of the certain location and provides direct information of the region of interest. Therefore, extracting the depth-resolved, i.e. local polarization properties, including retardation, of the tissue provides a more intuitive and accurate representation of the tissue structure and function. Throughout this disclosure, local or depth-resolved retardation are used interchangeably with birefringence and local or depth-resolved birefringence.

Though the local retardation properties can be solved recursively from the cumulated maps, this requires knowledge of the polarization state illuminating the sample and the polarization transformation caused by optical components in the detection path, which is often impractical, especially in case of catheter-based imaging. In some methods, the local retardation properties of the tissue can be resolved by using two or more measurements on the same tissue with different input polarization states. Commonly, this kind of PS-OCT system employs a polarization modulator to change the polarization state of the illuminating light sequentially in between the acquisition of depth profiles. Depth-resolved retardation maps can be obtained from the recorded fringes of a pair of sequential depth profiles with distinct polarization states, assuming the two profiles correspond to the same location in the tissue. Crucially, the precise polarization states of the illuminating light incident on the tissue after passing through system components do not have to be known. However, use of a modulator limits the imaging speed and laser source bandwidth, and increases the system complexity and cost. On the other hand, the embodiments described herein provide solutions for obtaining tissue local retardation measurements without the limitations of employing a modulator.

The methods and apparatus described here include the single input state single shot spectral domain PS-OCT scheme and a local birefringence extraction algorithm based on Stokes vector reasoning. The foregoing and other features and advantages are defined by appended claims. The following detailed description of exemplary embodiments, read in conjunction with the accompanying drawings is merely illustrative rather than limiting, the scope being defined by the appended claims and equivalents thereof.

Various embodiments disclose the construction of single input PS-OCT systems. Other embodiments disclose methods and apparatus for analyzing the local birefringence properties of a sample. A recently observed and confirmed physical phenomenon, named as the mirror state constraint, is described here, followed by a processing method relying on geometric reasoning in the Stokes domain and based on the mirror state constraint of local tissue birefringence properties that can be applied to data recorded with such an apparatus.

Thus, in one aspect the invention provides for a method for determining a retardance of a layer of a sample. The method includes: transmitting a first portion of a polarized light to a sample arm of an optical system and a second portion of the polarized light to a reference arm of the optical system; combining first return light returned from the sample arm and second return light from the reference arm; detecting, using a detector, the combined light along a first polarization state and a second polarization state to produce polarization data, the second polarization state being different from the first polarization state; determining, using a processor coupled to the detector, polarization states of light returning from upper and lower surfaces of a layer of the sample based on detecting the combined light; and determining, using the processor, a retardance of the layer of the sample based on the determined polarization states.

The polarization state of light backscattered by a retarding sample and measured along the same path used to illuminate the sample tends to align with a defined polarization state related to the input state. This offers a constraint in the evolution of the detected polarization states that helps to determine the sample retardation. This is useful in applications such as polarization sensitive optical coherence tomography (PS-OCT) to measure depth-resolved birefringence of a sample using a single illuminating polarization state. While previous implementations of PS-OCT have required the use of two multiplexed polarization states to illuminate the sample or a single known input polarization state in combination with complicated recursive reconstruction algorithms to determine the sample properties in a general sample with a layered architecture, the presently-disclosed methods overcome this limitation and enable depth-resolved birefringence imaging with a single input state PS-OCT system without requiring a specific known illuminating polarization state, and the methods are compatible with either fiber- or catheter-based imaging. Embodiments of the present invention provide single input state systems such as PS-OCT systems which have a lower cost, higher speed (since there is not a requirement for providing an input source having two multiplexed polarization states), and improved resolution compared to known systems, e.g. those using multiple input polarization states. Birefringence imaging has applications in fields such as ophthalmology, dermatology, intravascular imaging, or imaging of the gastrointestinal tract.

In an exemplary embodiment of the method, the method may further include determining a mirror state associated with the polarization data.

In another exemplary embodiment of the method, the mirror state may include a point on a Poincaré sphere.

In still another exemplary embodiment of the method, the mirror state may include an input polarization state with reversed helicity.

In yet another exemplary embodiment of the method, the layer of the sample may include a subsurface layer of the sample. The layer of the sample from which polarization information is obtained may be not just on an upper (or lower) surface of the sample but may include a subsurface layer, e.g. within the sample.

In another exemplary embodiment of the method, the optical system may include an optical coherence tomography system, wherein detecting the combined light along a first polarization state and a second polarization state further includes: detecting the combined light along a first polarization state and a second polarization state using the optical coherence tomography system. Use of an optical coherence tomography (OCT) system facilitates obtaining data from multiple layers within the sample.

In still another exemplary embodiment of the method, determining polarization states of light returning from upper and lower surfaces of a layer of the sample may further include: determining a rotation angle and a rotation axis of a rotation circle associated with the polarization states from upper and lower surfaces of the layer of the sample, and determining a retardance level and an apparent optic axis based on determining the rotation angle and the rotation axis, respectively. The disclosed method facilitates determining information such as rotation angle, rotation axis, retardance level, and apparent optic axis.

In yet another exemplary embodiment of the method, the sample may include a plurality of layers, and wherein determining a retardance of a layer of the sample based on the determined polarization states further includes: determining a retardance of each of the plurality of layers of the sample based on the determined polarization states, and wherein the method further includes: generating a reconstruction of the sample based on the retardance of each of the plurality of layers of the sample. The disclosed method facilitates generating a reconstruction based on retardance information obtained for each of the plurality of layers of the sample.

In another exemplary embodiment of the method, determining a retardance of a layer of the sample may further include: determining the retardance of the layer of the sample using the wavelength-dependence of the polarization states to reduce artifacts.

In another further exemplary embodiment of the method, determining the retardance of the layer of the sample using the wavelength-dependence of the polarization states to reduce artifacts may further include: determining the retardance of the layer of the sample using the wavelength-dependence of the polarization states to reduce artifacts based on spectral binning.

In still another exemplary embodiment of the method, the polarized light may include circularly polarized light.

In yet another exemplary embodiment of the method, the detector may include a first detector and a second detector, and wherein detecting the combined light along a first polarization state and a second polarization state to produce polarization data further includes: transmitting the combined light to a polarizing beam splitter, wherein the polarizing beam splitter transmits light having the first polarization state to the first detector and light having the second polarization state to the second detector. Two detectors may be used to collect data from the two different polarization states at the same time. A technical effect arising from using two separate detectors is that data from two different polarization states may be collected simultaneously, increasing the speed of data collection and overall throughput of the system.

In another exemplary embodiment of the method, the sample may include at least one of an ophthalmologic sample, a dermatological sample, an intravascular sample, or a gastrointestinal sample.

In a further exemplary embodiment of the method, the optical system may include a polarization sensitive optical coherence tomography (PS-OCT) system.

In another exemplary embodiment of the method, the optical system may be implemented using a free space optic system or a fiber optic system.

In another aspect the invention provides for an apparatus for determining a retardance of a layer of a sample. The apparatus includes: an interferometric optical system comprising a sample arm and a reference arm; a light source coupled to the optical system, the light source providing a first portion of a polarized light to the sample arm and a second portion of the polarized light to the reference arm, and the optical system combining first return light returned from the sample arm and second return light from the reference arm; a detector to detect the combined light along a first polarization state and a second polarization state to produce polarization data, the second polarization state being different from the first polarization state; and a processor coupled to the detector, the processor to: determine polarization states of light returning from upper and lower surfaces of the layer of the sample based on the detector detecting the combined light, and determine a retardance of a layer of the sample based on the determined polarization states.

In an exemplary embodiment of the apparatus, the processor may be further configured to: determine a mirror state associated with the polarization data.

In another exemplary embodiment of the apparatus, the mirror state may include a point on a Poincaré sphere.

In yet another exemplary embodiment of the apparatus, the mirror state may include an input polarization state with reversed helicity.

In still another exemplary embodiment of the apparatus, the layer of the sample may include a subsurface layer of the sample. The layer of the sample from which polarization information is obtained may be not just on an upper (or lower) surface of the sample but may include a subsurface layer, e.g. within the sample.

In another exemplary embodiment of the apparatus, the optical system may include an optical coherence tomography system, and wherein the processor, when detecting the combined light along a first polarization state and a second polarization state, is further configured to: detect the combined light along a first polarization state and a second polarization state using the optical coherence tomography system. Use of an optical coherence tomography (OCT) system facilitates obtaining data from multiple layers within the sample.

In still another exemplary embodiment of the apparatus, the processor, when determining polarization states of light returning from upper and lower surfaces of a layer of the sample, may further be configured to: determine a rotation angle and a rotation axis of a rotation circle associated with the polarization states from upper and lower surfaces of the layer of the sample, and determine a retardance level and an apparent optic axis based on determining the rotation angle and the rotation axis, respectively. The disclosed apparatus facilitates determining information such as rotation angle, rotation axis, retardance level, and apparent optic axis.

In yet another exemplary embodiment of the apparatus, the sample may include a plurality of layers, and wherein the processor, when determining a retardance of a layer of the sample based on the determined polarization states, is further configured to: determine a retardance of each of the plurality of layers of the sample based on the determined polarization states, and wherein the processor is further configured to: generate a reconstruction of the sample based on the retardance of each of the plurality of layers of the sample. The disclosed method facilitates generating a reconstruction based on retardance information obtained for each of the plurality of layers of the sample.

In still another exemplary embodiment of the apparatus, the processor, when determining a retardance of a layer of the sample, may further be configured to: determine the retardance of the layer of the sample using the wavelength-dependence of the polarization states to reduce artifacts.

In another exemplary embodiment of the apparatus, the processor, when determining the retardance of the layer of the sample using the wavelength-dependence of the polarization states to reduce artifacts, may further be configured to: determine the retardance of the layer of the sample using the wavelength-dependence of the polarization states to reduce artifacts based on spectral binning.

In yet another exemplary embodiment of the apparatus, the polarized light may include circularly polarized light.

In still another exemplary embodiment of the apparatus, the detector may include a first detector and a second detector, and wherein the apparatus is configured to transmit combined light to a polarizing beam splitter, wherein the polarizing beam splitter is configured to transmit light having the first polarization state to the first detector and light having the second polarization state to the second detector. Two detectors may be used to collect data from the two different polarization states at the same time. A technical effect arising from using two separate detectors is that data from two different polarization states may be collected simultaneously, increasing the speed of data collection and overall throughput of the system.

In another exemplary embodiment of the apparatus, the sample may include at least one of an ophthalmologic sample, a dermatological sample, an intravascular sample, or a gastrointestinal sample.

In still another exemplary embodiment of the apparatus, the optical system may include a polarization sensitive optical coherence tomography (PS-OCT) system.

In another exemplary embodiment of the apparatus, the optical system may be implemented using a free space optic system or a fiber optic system.

The foregoing and other aspects and advantages of the invention will appear from the following description. In the description, reference is made to the accompanying drawings which form a part hereof, and in which there is shown by way of illustration preferred embodiments of the invention. Such embodiments do not necessarily represent the full scope of the invention, however, and reference is made therefore to the claims herein for interpreting the scope of the invention.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which.

Panel (j) shows average local birefringence within the RNFL layer. Scale bars in panel (j) for panels (i)-(j), vertical: 400 µm, horizontal: 400 µm.

Figure 9:
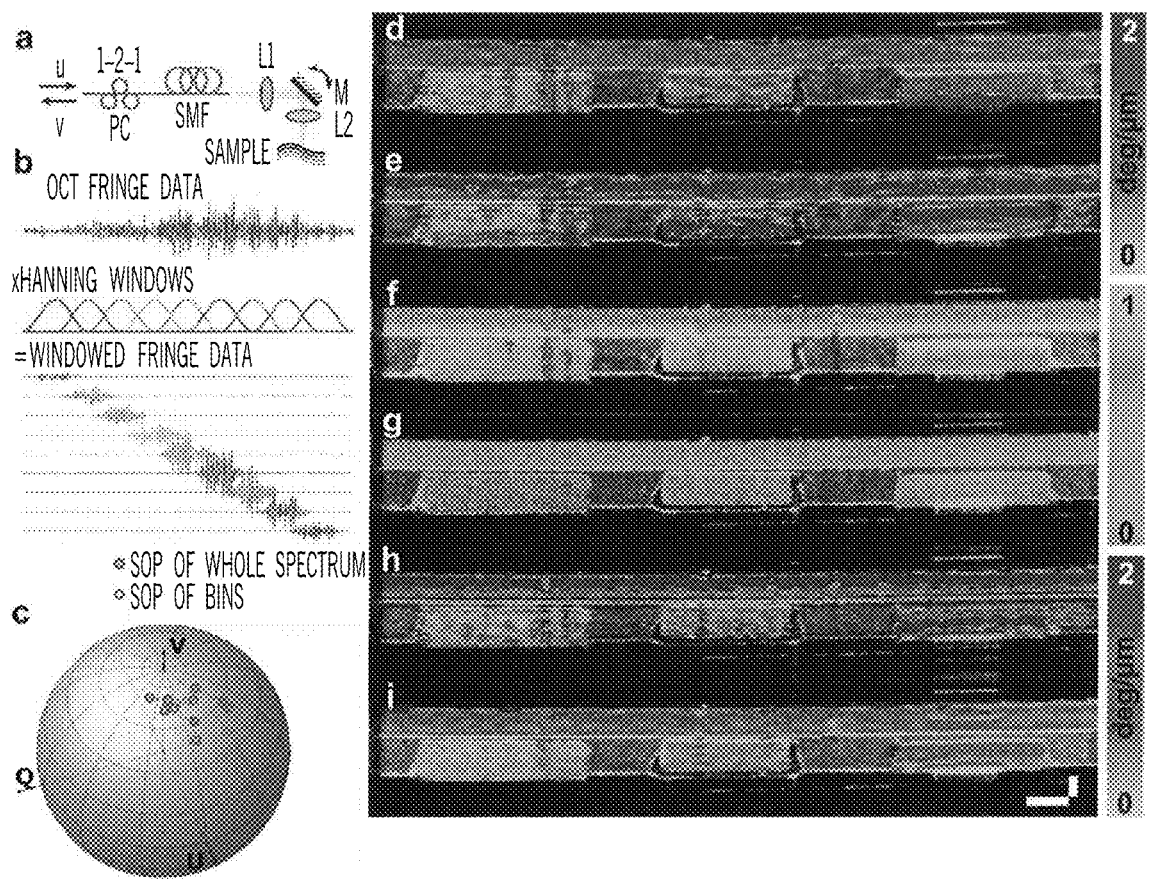

FIG. 9 shows a demonstration of the application of the mirror state constraint in a fiber-based system and the suppression of artifacts occurring from the alignment of the depth-dependent polarization state with the apparent optic axis with spectral binning.

Figure 10:
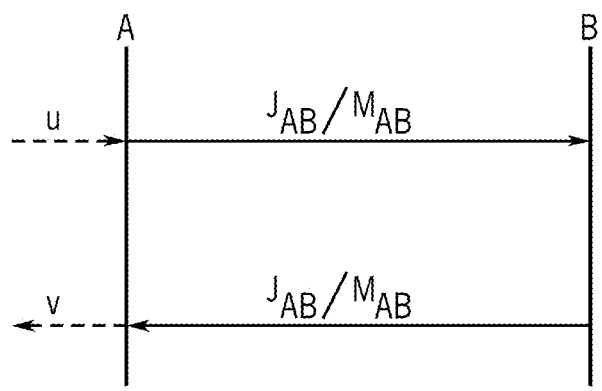

FIG. 10 shows a schematic diagram of the round-trip transmission through an element from A to B and back to A, described by the Jones and Mueller matrices, respectively.

Figure 11:
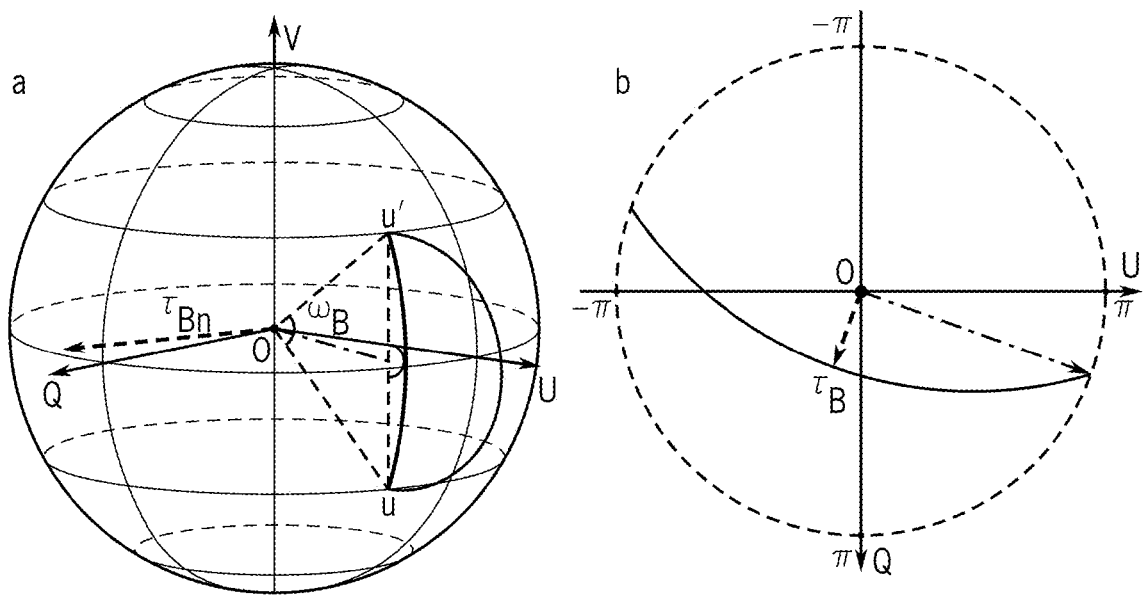

FIG. 11 shows the trace of the possible rotation vectors that map the input state u to its mirror state u'. Panel (a) shows the maximum and minimum rotation angle $\alpha$, $\beta$ and the corresponding rotation axes $\tau_{An}$, $\tau_{Bn}$ on the Poincare sphere. Panel (b) shows that $\tau_{An}$ and $\tau_{Bn}$ define the orientation and curvature of the trace of the possible rotation vectors (red line).

Figure 12:
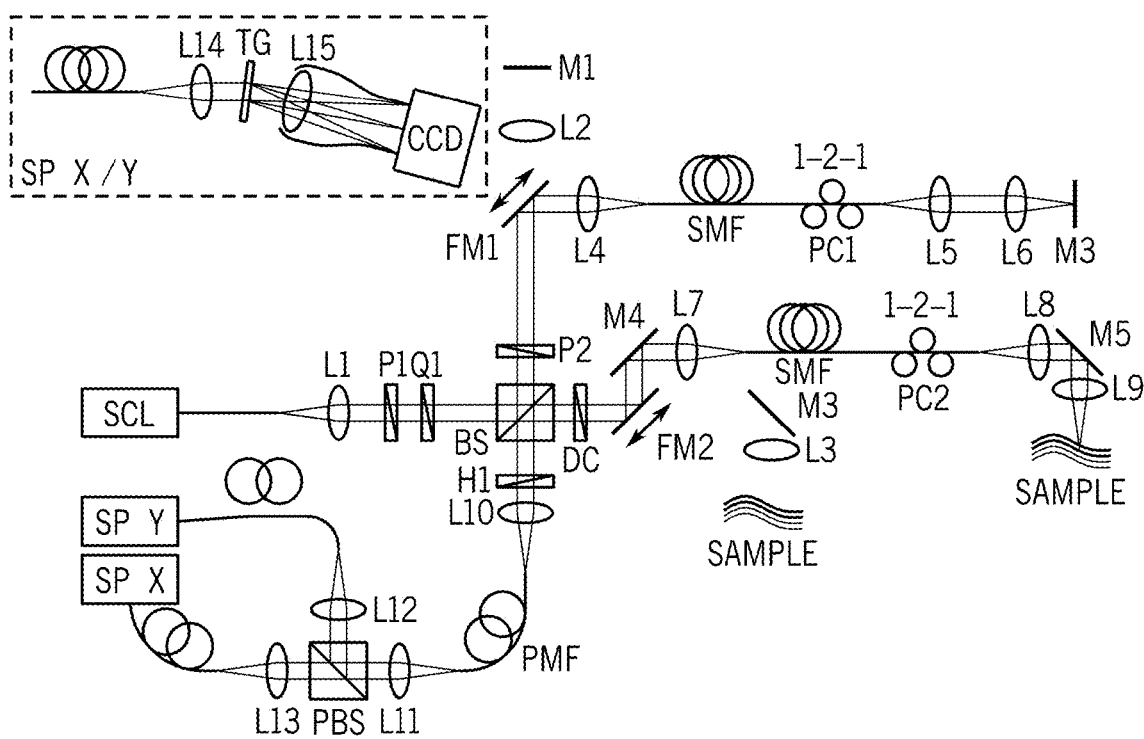

FIG. 12 shows a setup that may be used in various embodiments disclosed herein.

Figure 13:
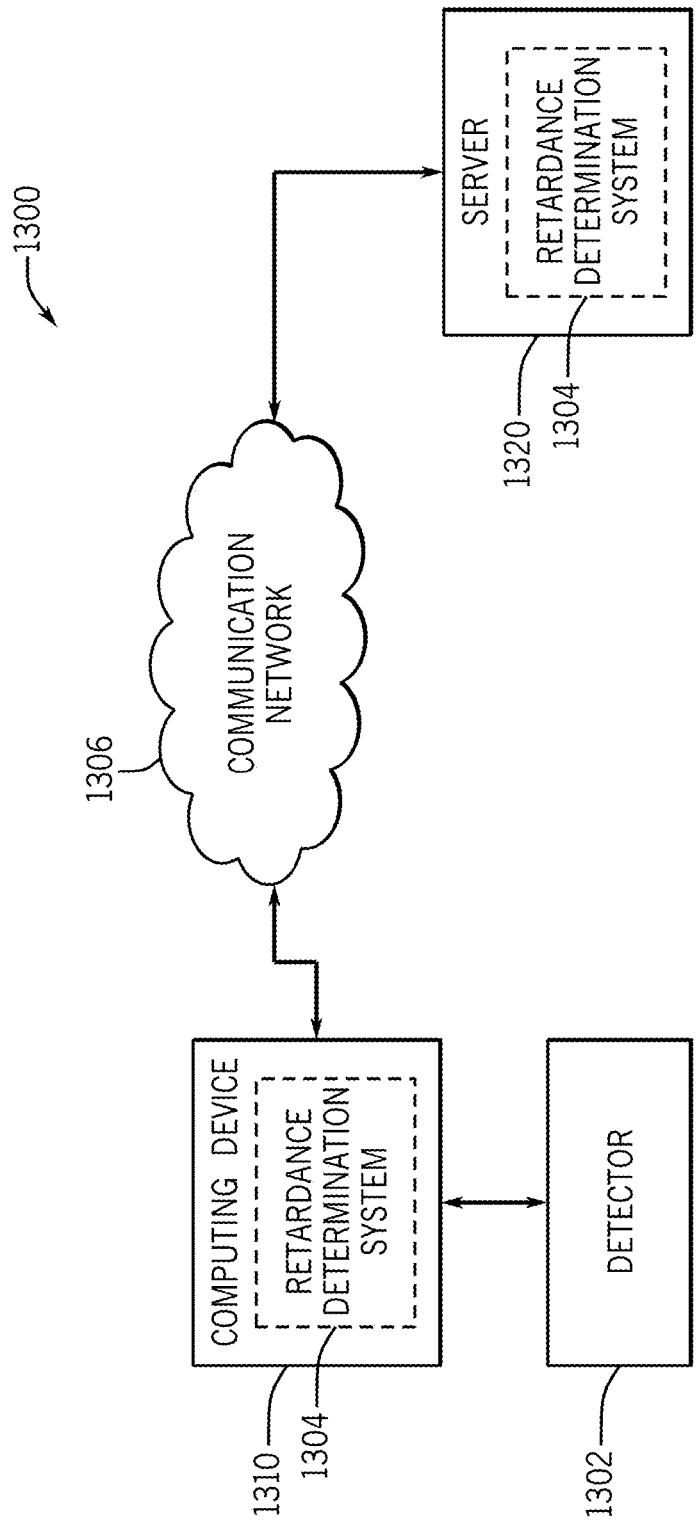

FIG. 13 shows an example of a system for determining a birefringence of a layer of a sample in accordance with some embodiments of the disclosed subject matter.

Figure 14:
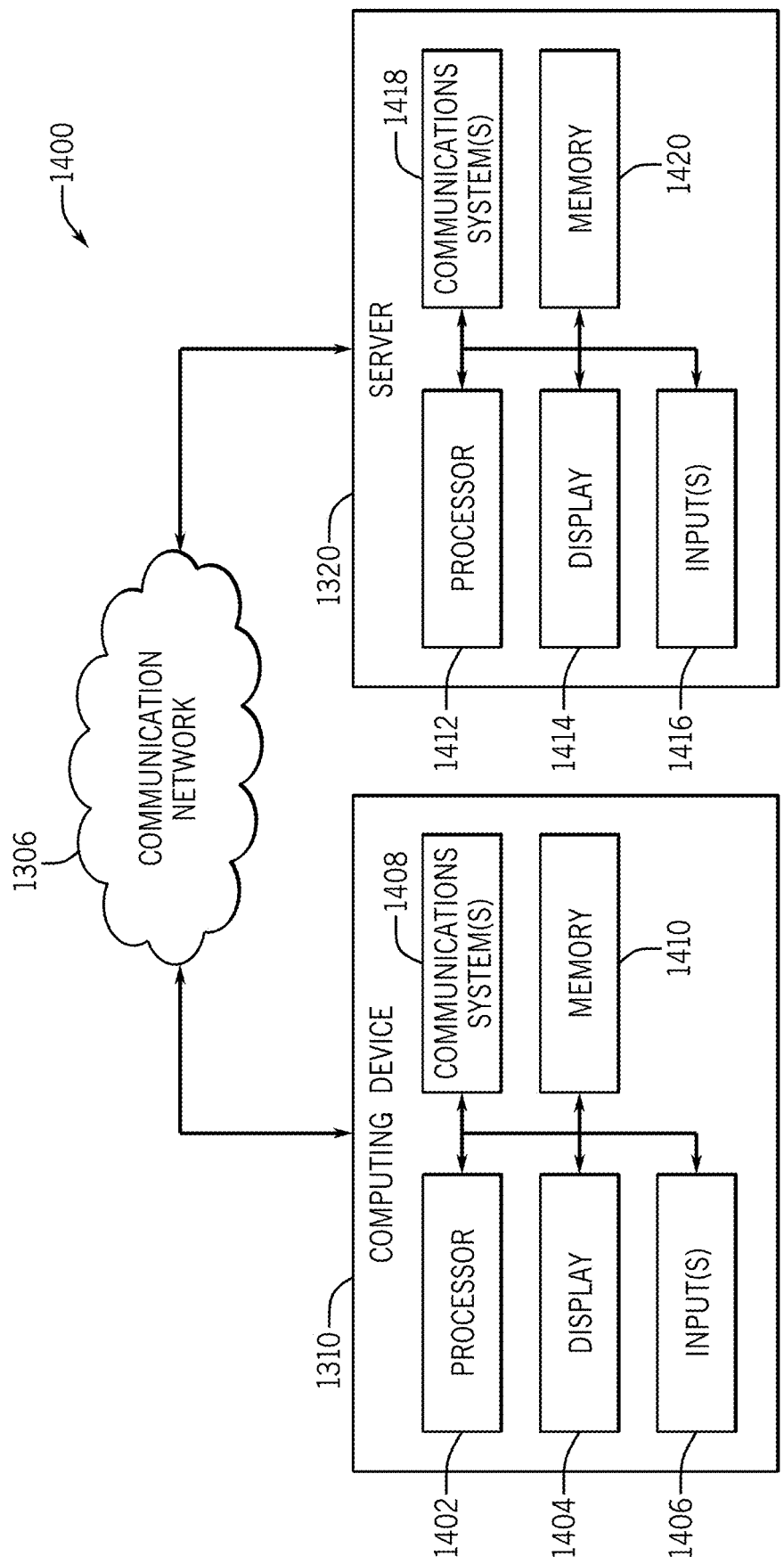

FIG. 14 shows an example of hardware that can be used to implement a computing device and server in accordance with some embodiments of the disclosed subject matter.

Figure 15:
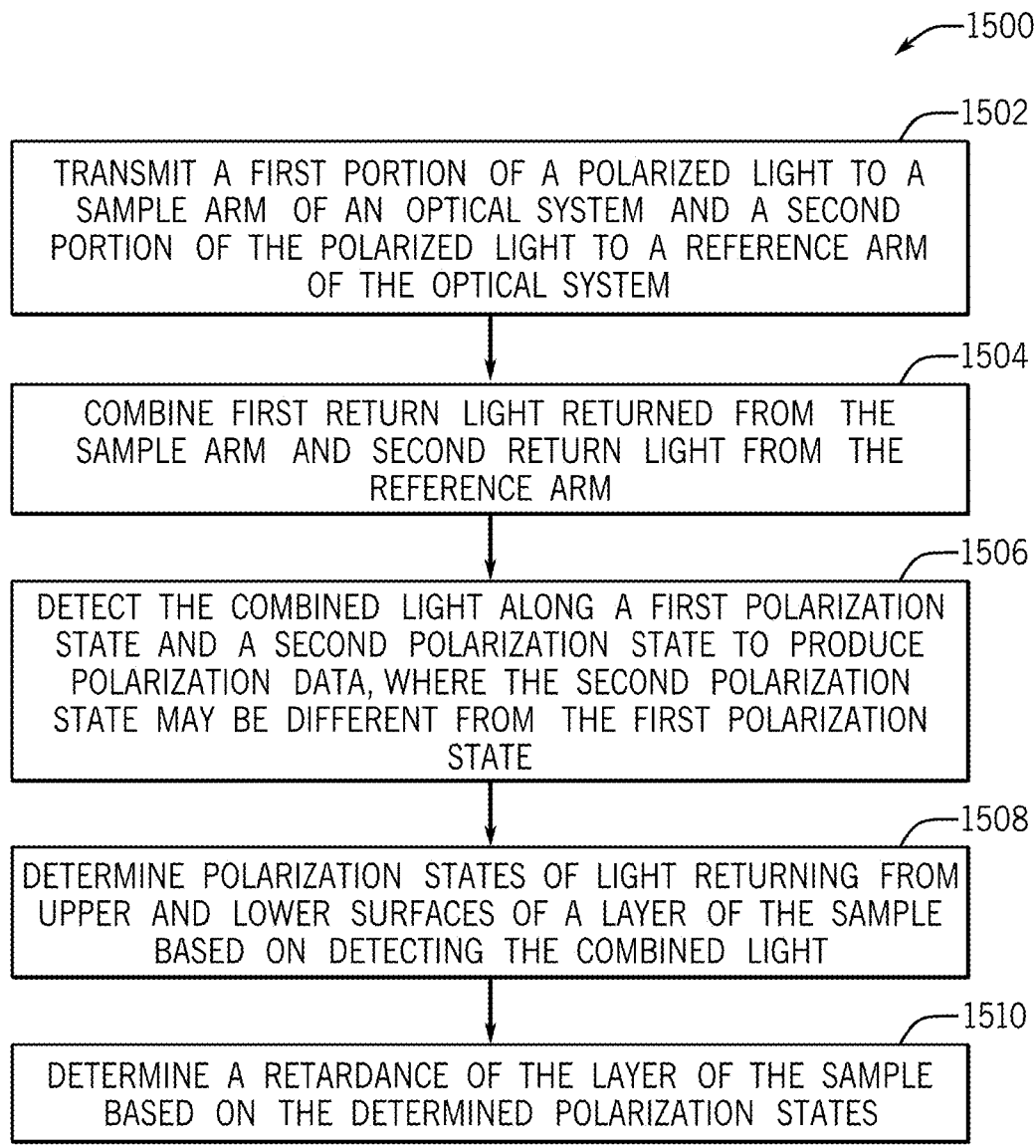

FIG. 15 shows an example of a process for determining a birefringence of a layer of a sample in accordance with some embodiments of the disclosed subject matter.

DETAILED DESCRIPTION OF EXEMPLARY EMBODIMENTS

Thus, the present application discloses embodiments of systems and methods for obtaining birefringence information of the sample which are capable of providing the local birefringence information rather than the cumulated birefringence information. Optical fiber-based implementations are more preferable in endoscopic and intravascular imaging. Free space bulk optics implementation is more suitable for ophthalmological imaging.

For this invention, modifications of the laser source device of the subject application are illustrated by means of examples of free space optical devices being part of an apparatus for optical coherence tomography, although those skilled in the art will understand that embodiments may be implemented with the use of fiber optics elements, and may be used as independent devices.

The polarization state of light backscattered by a retarding sample and measured along the same path used to illuminate the sample tends to align with a defined polarization state related to the input state. This offers a constraint in the evolution of the detected polarization states that helps to determine the sample retardation. This is useful in polarization sensitive optical coherence tomography (PS-OCT) to measure depth-resolved birefringence of a sample using a single illuminating polarization state.

In contrast, previous implementations of PS-OCT have required two multiplexed polarization states to illuminate the sample or a single known input polarization state in combination with complicated recursive reconstruction algorithms to determine the sample properties in a general sample with a layered architecture. The present invention overcomes this limitation and enables depth-resolved birefringence imaging with a single input state PS-OCT system without requiring a specific known illuminating polarization state, compatible with fiber- and catheter-based imaging.

Embodiments of the present invention provide single input state PS-OCT systems which have a lower cost than more complex systems using multiple input polarization states. Birefringence imaging with PS-OCT has applications in fields such as ophthalmology, dermatology, intravascular imaging, or imaging of the gastrointestinal tract.

Figure 1:
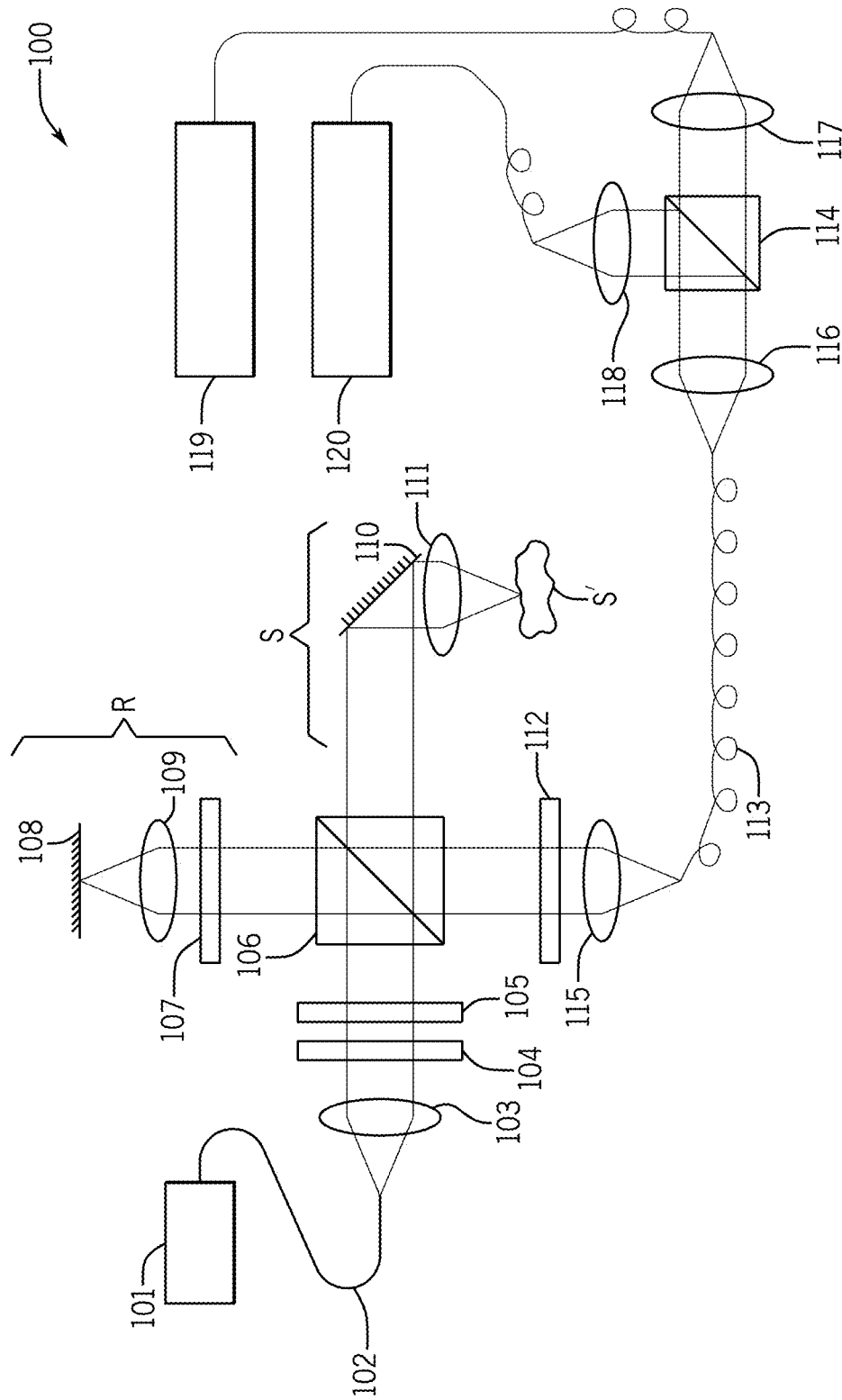
FIG. 1 is a schematic diagram of a single input state single shot free space spectral domain polarization sensitive optical coherence tomography system, in accordance with one embodiment.

FIG. 1 shows a block diagram of an embodiment of a free space optics-based single input state single shot PS-OCT system 100; as noted above, in various embodiments the same principles may be used to implement a fiber-based PS-OCT system. The light source element 101 illustrated in FIG. 1, may include one or more lasers tuned to a variety of spectral bands. A light beam from the source element 101 may be coupled into a single mode fiber 102 by a lens 103, and passed through a polarizer 104 and a quarter wave plate 105, thereby becoming circularly polarized. The light beam is then split into the "reference arm" (labeled R in FIG. 1) and "sample arm" (labeled S in FIG. 1) by a non-polarizing beam splitter 106. In the reference arm R, the light beam passes a polarizer 107 and is relayed to a reflector 108 by a lens 109 and is reflected back through the same path. In the sample arm S, a scanning mirror 110 and an objective 111 define the scanning system, laterally moving a light spot generated by the light beam over sample S'. The beams reflected from the reference arm R and backscattered from the sample arm S are recombined at the beam splitter 106 and detected by a polarization sensitive detection scheme, comprising a half wave plate 112, a piece of polarization maintaining fiber 113 and a polarizing beam splitter 114, four collimation lenses 115-118 and two high speed spectrometers 119 and 120.

Figures 2A, 2B:
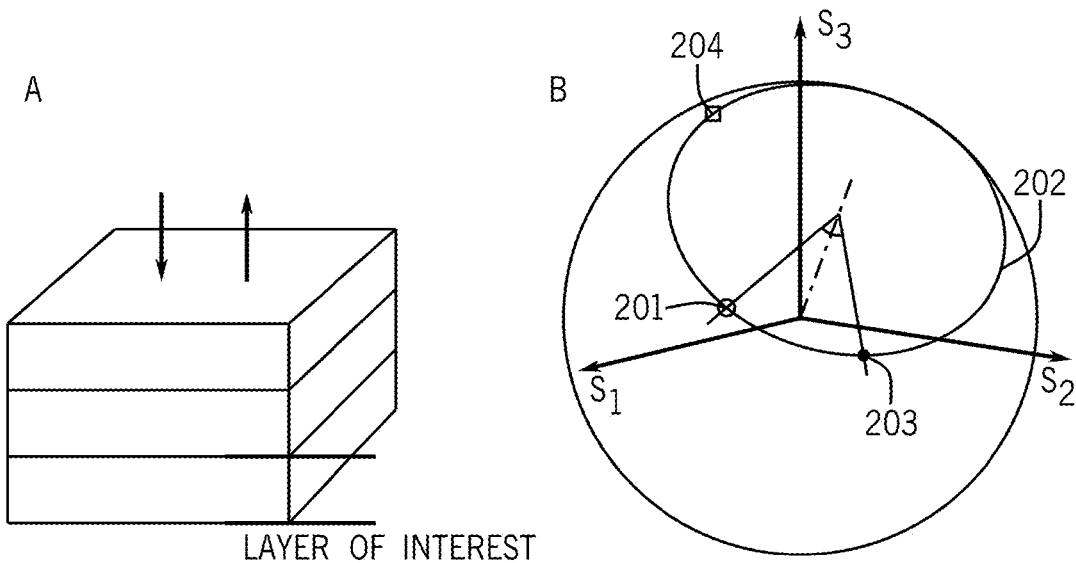
FIG. 2 depicts a sample consisting of multiple layers with distinct birefringence properties, and the principle of the observed constraint in the evolution of the detected polarization states.

In another embodiment, which may be carried out in conjunction with the free-space PS-OCT embodiment outlined above, FIGS. 2A and 2B depict a data processing method of a single input state polarization sensitive OCT hardware configuration for extraction of local tissue birefringence properties. However, the hardware configuration and data processing method do not necessarily need to be used in the same implementation and in various embodiments may be used independently of one another.

FIGS. 2A and 2B depict the geometric reasoning of local birefringence using the mirror state constraint, which is described in greater detail below. The reasoning is explained in Stokes domain polarimetry, but can also be expressed in Jones formalism. The mirror state constraint is based on a recent observation made by our group about the evolution of light polarization states in a birefringent sample, namely: for a sample having stacked layers with random homogeneous birefringence (no diattenuation), the evolution of the backscattered polarization states as a function of depth includes connected but discontinuous arcs lying on the Poincare sphere. In a transpose-symmetric system, the circles that the arcs are lying on all pass through the "mirror state", which is the QU plane reflection of the input polarization state, corresponding to the input polarization state with reversed polarization helicity. Application of this constraint involves determining the "mirror state" to estimate the birefringence rotation circle on the Poincare sphere between the polarization states reflected from the top and bottom surface of a thin sample layer of interest. By knowledge of the rotation circle, the rotation axis and rotation angle can be obtained, corresponding to the apparent optic axis and birefringence level, respectively, for the layer of interest.

An exemplary sample is shown in FIG. 2A, which contains three layers having distinct optic axes. The round-trip polarization states' evolution in the sample layer of interest is shown in FIG. 2B. For this example, it is assumed that the layer of interest is the third layer, which is the lowest/deepest of the three layers and is labeled in FIG. 2A. As indicated in FIG. 2B, the polarization states 201 and 203 are measured from the light backscattered from the upper and lower surfaces of the layer of interest. With the mirror state 204, a rotation circle 202 is constructed, which is the birefringence rotation circle of the layer of interest. Specifically, the rotation angle is the local retardation and the rotation axis is the apparent optic axis.

Table 1 describes individual steps of the data processing method to recover depth-resolved birefringence information from measurements with a single input state PS-OCT system. In various embodiments, the spectral interference fringes recorded by spectrometers 119 and 120 are pre-processed with algorithms that are typically used in conventional Fourier domain OCT, including steps such as background subtraction, k-space resampling, and/or dispersion compensation. The pre-processed fringes from spectrometers corresponding to a scan of the x-y plane are denoted as $H(x, y, \lambda)$, $V(x, y, \lambda)$.

TABLE 1

| | |
|---|---|
| Step 1 | Obtain pre-processed fringes $H(x, y, \lambda)$, $V(x, y, \lambda)$ from the spectrometers 119 and 120 in FIG. 1. |
| Step 2 | Calculate the depth field profiles $E_H(x, y, z)$, $E_V(x, y, z)$ and depth intensity profile $I(z)$. $$\begin{cases} E_H(z) = F(H(\lambda)) \\ E_V(z) = F(V(\lambda)) \end{cases}$$ $$I(z) = E_H(z)E_H^*(z) + E_V(z)E_V^*(z)$$ where $F(\ )$ is the Fourier transform and * indicate complex conjugation. |
| Step 3 | Calculate the depth resolved Stokes Parameters $S(x, y, z)$ $$\begin{bmatrix} S_1 \\ S_2 \\ S_3 \end{bmatrix} = \begin{bmatrix} |E_H(x, y, z)|^2 - |E_V(x, y, z)|^2 \\ 2\,real(E_H(x, y, z)E_V^*(x, y, z)) \\ -2\,imag(E_H(x, y, z)E_V^*(x, y, z)) \end{bmatrix}$$ |
| Step 4 | Perform incoherent averaging in Stokes domain $S_{avg}(x, y, z) = S(x, y, z) \otimes k(x, y, z)$ where $k(x, y, z)$ is the averaging kernel. |
| Step 5 | Perform Stokes normalization $S_{avg}(x, y, z) = S_{avg}(x, y, z)/|S_{avg}(x, y, z)|$ |
| Step 6 | Retardation reasoning $S_{OA} = (S_n(x, y, z - \Delta z) - S_n(x, y, z + \Delta z)) \times (S_{mirror\ point} - (S_n(x, y, z - \Delta z))$ where $S_{mirror\ point}$ is the mirror state of the system. $$S_A = \frac{S_{OA}}{|S_{OA}|} * \cos[\angle(S_{OA}, S_n(x, y, z + \Delta z))]$$ where $\angle(,\ )$ represents the acute angle between two vectors. $r(x, y, z) = \angle((S_n(x, y, z - \Delta z) - S_A(x, y, z), S_n(x, y, z + \Delta z) - S_A(x, y, z))$ Where $r(x, y, z)$ is the local retardation, i.e. the retardance accrued over the distance $2\Delta z$, expressed in angle per distance. |

Figure 3:
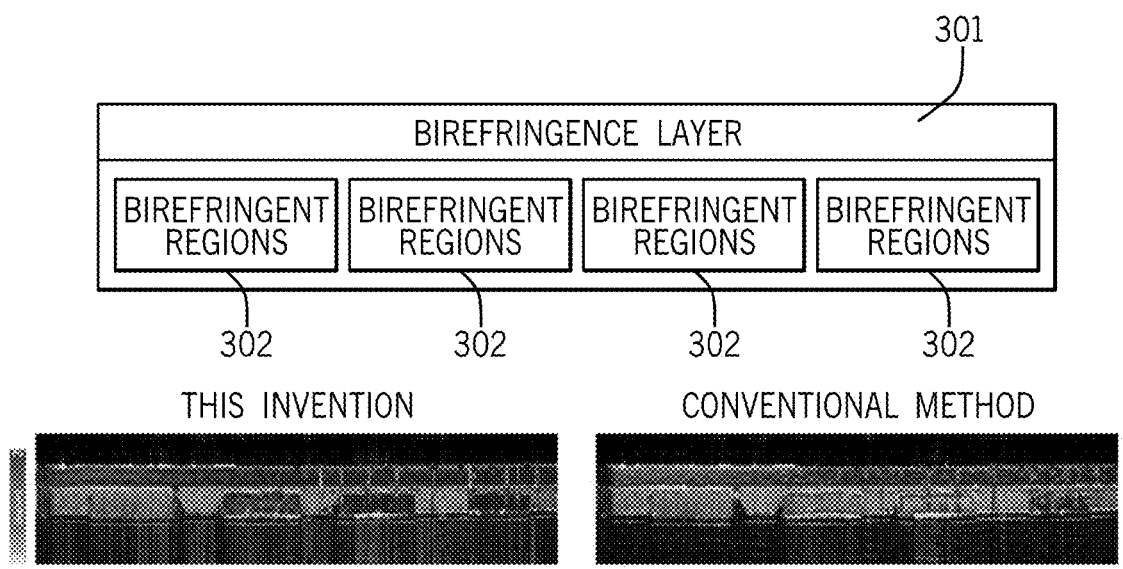
FIG. 3 shows a birefringence image of a phantom with layers of distinct birefringence, demonstrating the improved sensing capability of the proposed method as compared to conventional reconstruction strategies.

A birefringence phantom with layers and regions of distinct optic axis orientation and birefringence is imaged and, as shown in FIG. 3 (top), the birefringent regions 301 and 302 have different optic axes. A conventional single input state PS-OCT implementation (lower right panel) is unable to resolve the true local birefringence of a region which is below a birefringent layer. However, using an embodiment of the present invention (lower left panel), the true birefringence can be identified within the phantom.

Figure 4:
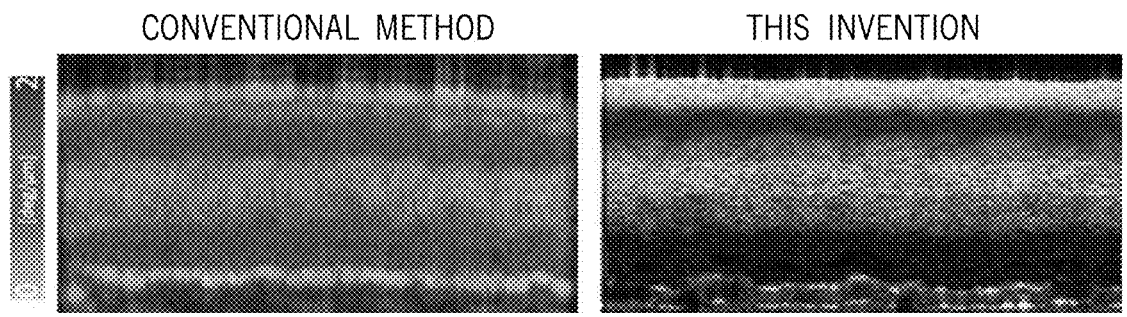
FIG. 4 shows a comparison of birefringence in a layered phantom measured with the proposed method and conventional two input state PS-OCT.

Embodiments of the invention can provide higher resolution images with the same contrast as current state of the art two-input state PS-OCT. In general, the costs associated with apparatus that are implemented in accordance with this invention are significantly lower than current devices and such apparatus are able to provide resolution that is not limited by the polarization modulator. For example, FIG. 4 shows a same phantom imaged by two-input PS-OCT (left panel) and the present invention (right panel). In addition, embodiments of the present invention enable local birefringence contrast with single input state single shot polarization sensitive OCT. Known single input PS-OCT procedures do not reconstruct the local birefringence contrast but instead provide the cumulative birefringence contrast, which fails to visualize valuable local tissue structural information.

Polarization offers a compelling contrast mechanism for diverse applications from remote sensing to biomedical optics. Conventionally, multiple input polarization states are required to fully characterize the polarization properties of a sample. It was observed that the polarization state of backscattered or reflected light, when measured through identical illumination and detection paths, frequently aligns with the employed input polarization state 'mirrored' by the horizontal plane of the Poincaré sphere. Here, we explore the predisposition for this mirror state and demonstrate how it constrains the depth-dependent evolution of polarization states measured with polarization sensitive optical coherence tomography (PS-OCT), thereby enabling analysis of depth-resolved tissue birefringence even when using a single input polarization state.

Figure 5:
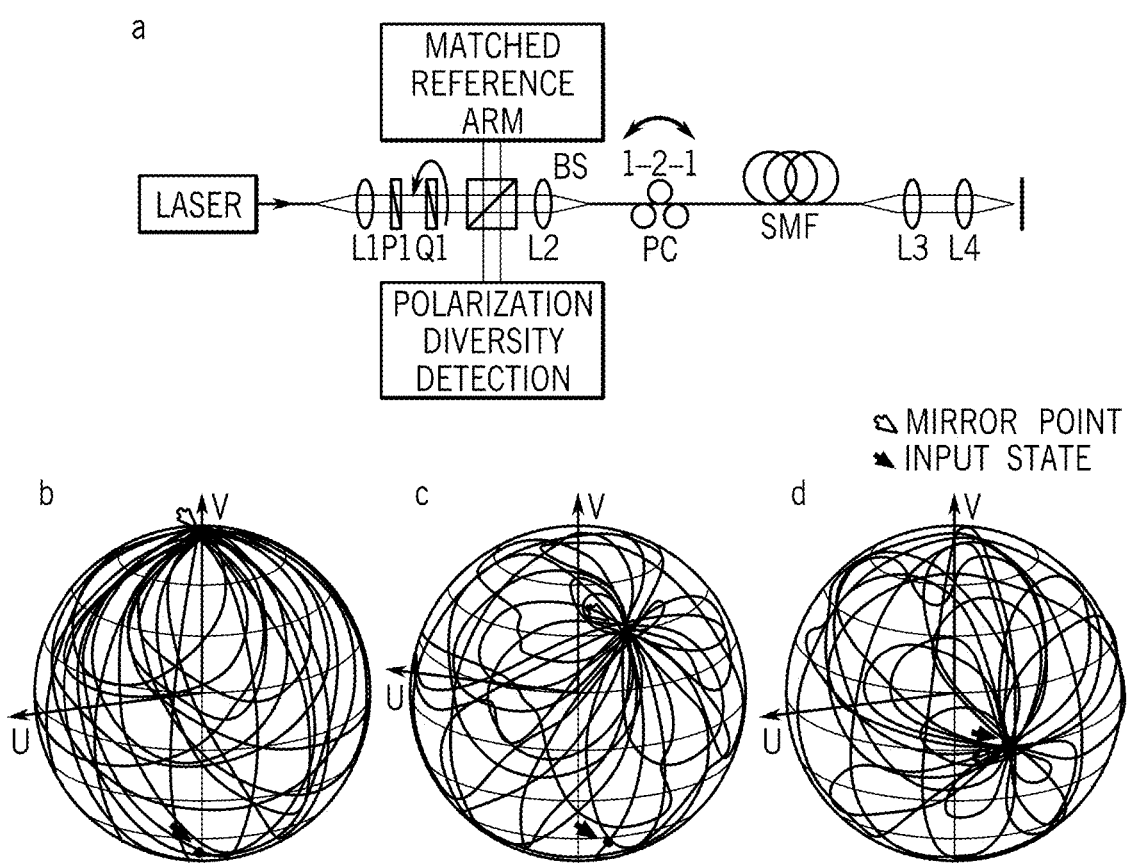
FIG. 5 shows a demonstration of the polarization mirror state. Panel (a) shows a schematic drawing of the employed optical system. L1-4: lenses, M: mirror, P1: polarizer, PC: polarization controller, Q1: quarter wave plate, SMF: single mode fiber. Panels (b)-(d) show polarization state evolution on the Poincare sphere as a result of moving the three paddles of the PC when using circularly, elliptically and linearly polarized input states, respectively, indicated by the blue arrows. The polarization mirror state manifests by the repeated crossing of the polarization state evolution in a specific point, highlighted by the red arrow in each Poincare sphere.

Earlier investigations of the polarization properties of single mode fibers reported on aspects of the polarization mirror state, yet without elucidating its manifestation. To examine the polarization mirror state, we measured the round-trip signal through a 1.5 m long single-mode optical fiber, as depicted in FIG. 5. Employing a polarization controller to alter the birefringence of the fiber, we measured the time-varying polarization state resulting from randomly moving the paddle positions of the controller. Visualized as a normalized Stokes vector in the Q, U, and V-coordinates of the Poincare sphere, the polarization state distinctly evolves multiple times through a specific state u' (FIG. 5, panel (b)). Repeated with different launching polarization states u, which were measured by reflecting the light to the detector before entering the fiber, we identify the state u'=D·u, where D=diag(1,1,−1), as the input state mirrored by the horizontal QU-plane, and designate it as the polarization mirror state (FIG. 5, panels (c), (d)). Of note, all measurements were performed in the fixed coordinates of the receiver and are independent of the orientation of the coordinates in the illumination path.

Figure 6:
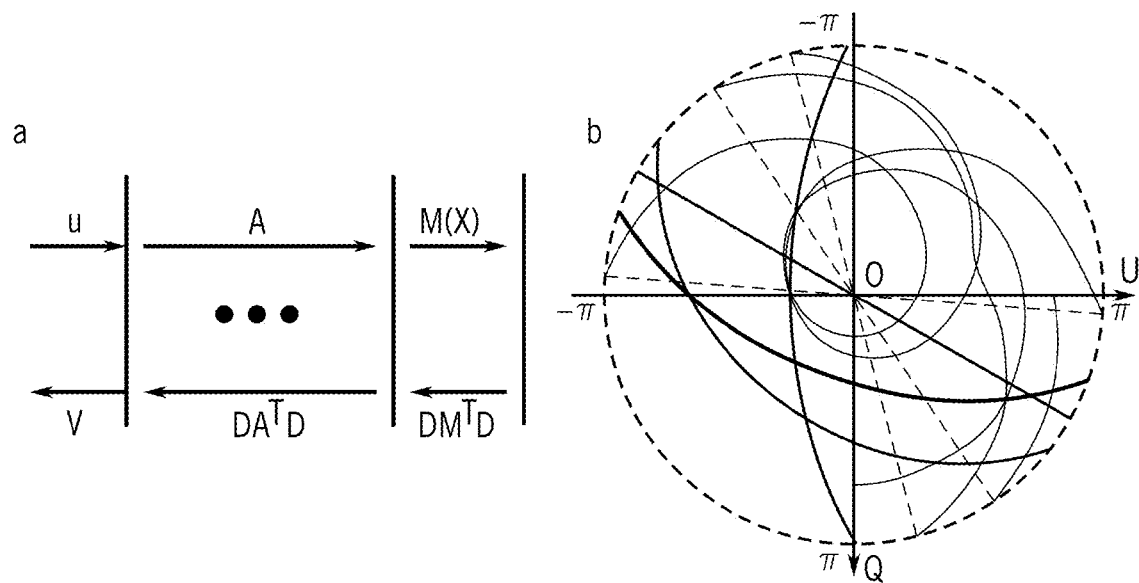
FIG. 6 shows a theoretical explanation of the polarization mirror state. Panel (a) shows a model of the round-trip propagation through a reciprocal sample, comprising M(x) with varying birefringence and a static element A. Panel (b) shows that the rotation vectors of all linear retarders localize within a circle of radius $\pi$ within the QU-plane of the Poincare sphere. The green trace represents the simulated rotation vector evolution for a synchronous movement of the polarization controller paddles. The blue curves represent the rotation vectors of $D \cdot A^T \cdot M^T(x) \cdot D \cdot M(x) \cdot A$ for M(x) with linearly increasing retardation, for three representative sets of distinct A and M(x). The red curve represents the end points of the rotation vectors mapping the randomly chosen input polarization state $[x,y,z]^T$ exactly to its mirror state. Every crossing of the green and blue lines with the red line correspond to the evolution of the polarization state through the mirror state.

To appreciate the mirror state phenomenon, we consider a general retarder M(x) with its retardation varying as a function of x, e.g. the polarization controller's paddle positions. It may be preceded by a static element A. The combined system, illustrated in FIG. 6, panel (a), transforms the input polarization state u into the output state v:

$$v = D \cdot A^T \cdot M^T(x) \cdot D \cdot M(x) \cdot A \cdot u = P(x) \cdot u. \quad (1)$$

Here, $P = D \cdot A^T \cdot M^T \cdot D \cdot M \cdot A$, and all vectors and matrices are in the rotation group SO(3). We chose to follow the convention of maintaining the orientation of the spatial xy-coordinates irrespective of the light's propagation direction. In reciprocal media, the reverse transmission through element M is described by $D \cdot M^T \cdot D$ (see below). It is important to note that the roundtrip transmission P is D-transpose symmetric $P = D \cdot P^T \cdot D$, which makes P a linear retarder. The round-trip effectively cancels any optical activity or circular retardation. The effect of P on the input state can be described by a rotation vector ω(P) lying in the QU-plane of the Poincaré sphere, with its direction indicating the rotation axis, and its length defining the amount of rotation. Considering their 2π-ambiguity, the rotation vectors of all possible linear retarders are confined to a circle with a radius of π within the QU-plane (FIG. 6, panel (b)). When moving the polarization controller paddles, ω(P) traces out an intricate path in the QU-plane, as shown by the green line in FIG. 6, panel (b) for simulation of a synchronous movement of the three paddles.

There exists only a single rotation vector within the QU-plane that rotates a given input state u onto an arbitrary output state v. This rotation vector is defined by the intersection of the QU-plane and the plane bisecting u and v. In order for u to pass through v, ω(P) has to evolve through this specific point within the π-circle of the QU-plane. The only exception is that there exists a continuum of rotation vectors that map u onto its mirror state u'=D·u, because the QU-plane coincides with the bisecting plane in this case. The rotation vectors are located on a curve r within the QU-plane (red curve in FIG. 6, panel (b); see below for further information). Every intersection of ω(P) with r corresponds to v evolving through the mirror state u', explaining its frequent realization.

We next used PS-OCT to measure the polarization state of light backscattered within a scattering sample as a function of its round-trip depth. At the scale of the spatial resolution of OCT, tissue can be modeled as a sequence of homogeneous linearly birefringent layers with distinct optic axis orientations. M(x) now describes a linear retarder with a retardance that linearly increases with depth x, resulting in $D \cdot M^T \cdot D = M$. The parameter A describes the combined effect of system components and preceding tissue layers. The resulting rotation vectors ω(P) describe regular curves across the π-circle (blue curves in FIG. 6, panel (b)). All possible traces intersect the curve r precisely once, ensuring periodic crossing of u'. To inspect in more detail the evolution of v, we take its derivative with respect to x, and substitute $u = P^T(x) \cdot v$:

$$\frac{\partial v}{\partial x} = \frac{\partial P(x)}{\partial x} \cdot P^T(x) \cdot v = \tau(x) \times v. \quad (2)$$

Because $P \cdot P^T = I$, $(\partial P/\partial x) \cdot P^T = -P \cdot (\partial P^T/\partial x)$ is skew-symmetric and can be expressed as the cross-product operator τx, which is constant for a retardance that linearly increases with x (see below for further information). Accordingly, v evolves on the Poincaré sphere with constant speed on a circle passing through u'.

Figure 7:
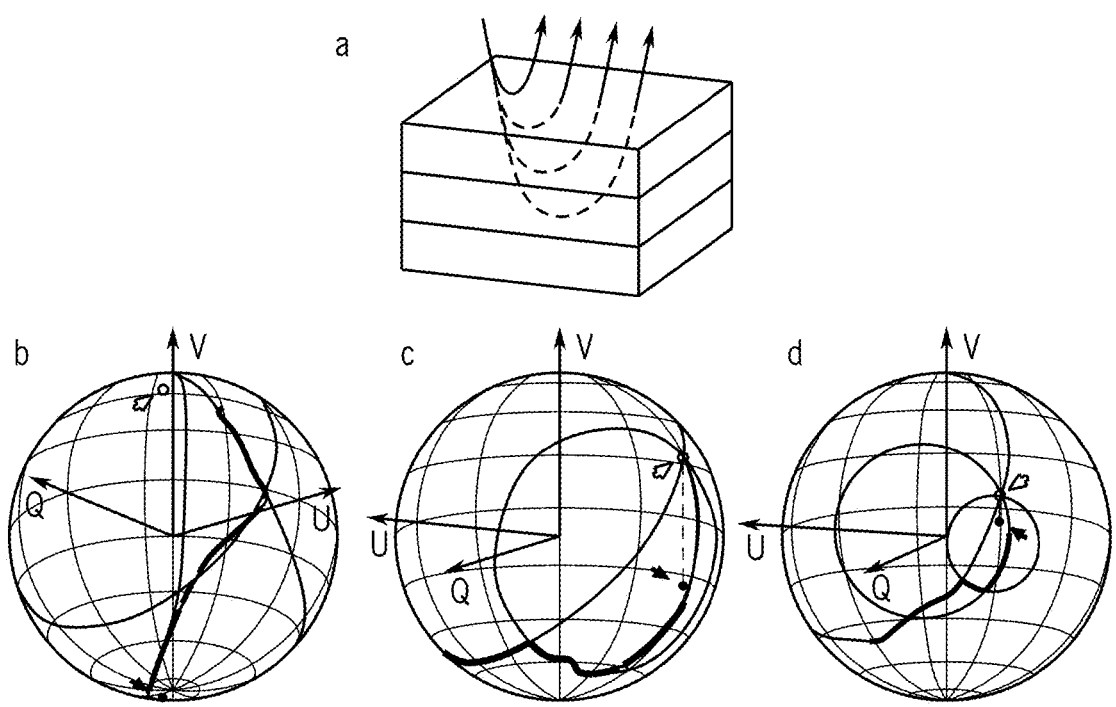
FIG. 7 shows the experimental evolution of coherence-gated polarization states in a three-layer birefringence phantom. Panel (a) shows a schematic sketch of the phantom with color-coded layers, each featuring a distinct optic axis orientation. Panels (b)-(d) show a polarization state evolving trace (color-coded corresponding to panel (a)) for each layer on the Poincare sphere with different input polarization state (panel (b) shows circularly polarized input light; panel (c) shows elliptically polarized input light; panel (d) shows linearly polarized input light). Purple lines are the fitting circles of the polarization state evolution of each phantom layer. Mirror state and input polarization state are indicated by red and blue arrows, respectively. It can be noticed that the mirror state and input state are symmetric with respect to the QU plane, corresponding to light with reversed polarization helicity.

For experimental validation, we prepared a scattering phantom consisting of three linearly birefringent layers with distinct optic axis orientations (FIG. 7, panel (a)). FIG. 7, panels (b)-(d) show the depth-dependent polarization states measured with PS-OCT for three distinct input polarization states. Fitting circles to the polarization state evolution within each layer demonstrates a close match and all circles evolve through the polarization mirror state u', as expected.

A persistent challenge in single-input-state PS-OCT is to measure the sample's local retardation, i.e. the derivative of the retardance of P(x) with depth, which is given by the norm of |τ| and is proportional to the sample birefringence. Following Equation (2) we have $$\left| \frac{\partial v}{\partial x} \right| = |\tau| \sin \alpha, \quad (3)$$

where we used |v|=1. α is the angle between the rotation vector τ and the polarization state v and is needed to deduce local retardation. Owing to the evolution of v through u', both δv/δx and (v−u') lie within the same plane orthogonal to τ. Hence, the direction can be obtained by the cross-product $\tau_0 = (\delta v/\delta x) \times (u'-v)$, and $\sin \alpha = |\tau_0 \times v|/|\tau_0|$, allowing to calculate, after some algebraic manipulations:

$$\tau = \frac{\frac{\partial v}{\partial x} \times (u' - v)}{1 - v^T \cdot u'}. \quad (4)$$

Figure 8:
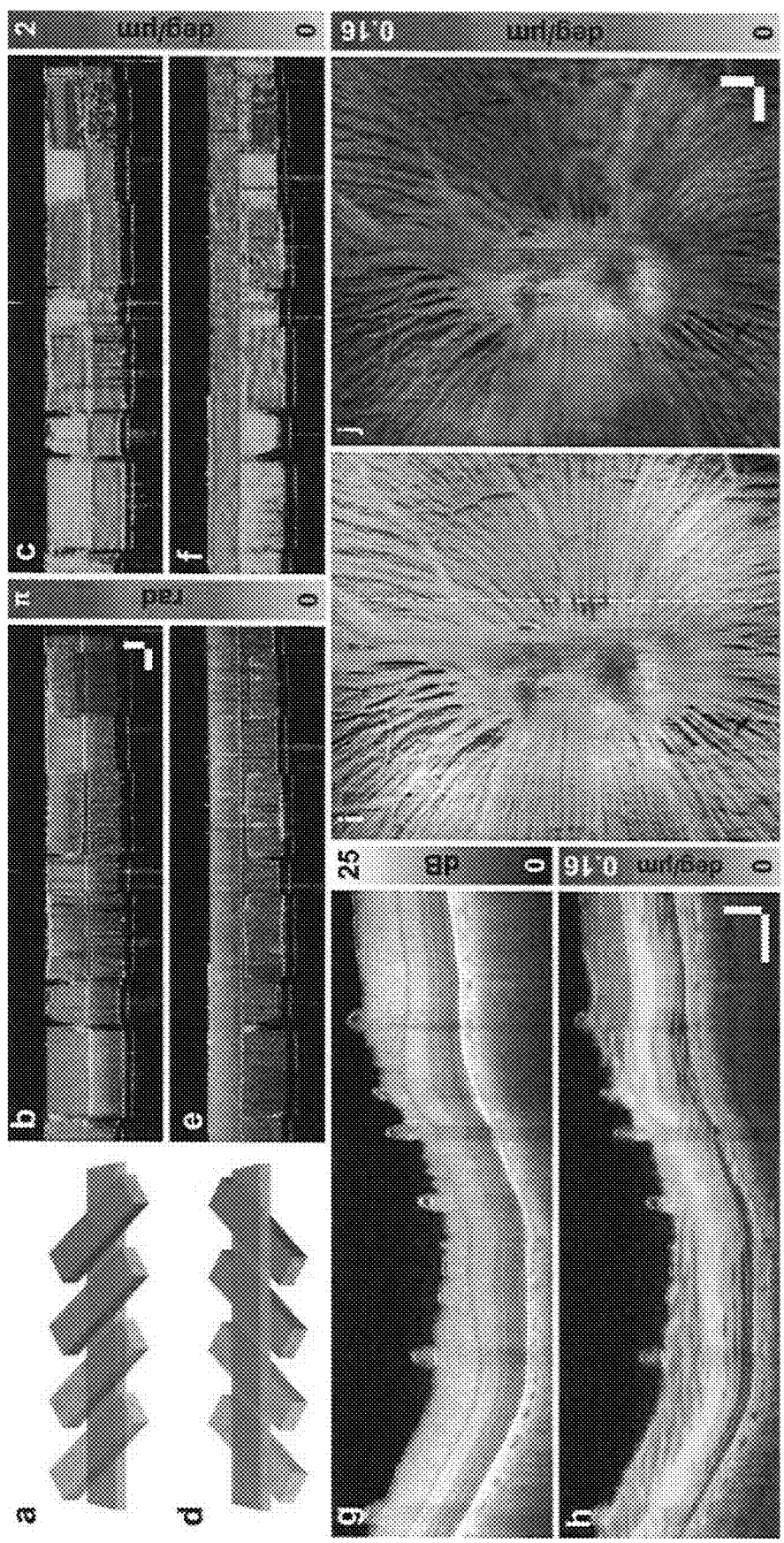
FIG. 8 shows intensity and birefringence images of phantom and swine retina. Panels (a)-(c) show a schematic sketch, cumulative retardation image and local retardation image of the two-layer phantom sample, respectively. Panels (d)-(f) show a schematic sketch, cumulative retardation image and local retardation image of the flipped phantom sample, respectively. Scale bars in panel (b) for panels (b)-(c) and panels (e)-(f), vertical: 100 µm, horizontal: 400 µm. Panel (g) shows a cross-sectional intensity image of swine retina. Panel (h) shows a cross-sectional local birefringence image of swine retina reconstructed using the polarization mirror state. Scale bars in panel (h) for panels (g)-(h), vertical: 100 µm, horizontal: 400 µm. Panel (i) shows an en face intensity projection of the RNFL layer of swine retina. The yellow dashed line indicated the position of the cross-sectional images shown in panels (g) and (h).

To validate the ability of the polarization mirror state to reconstruct local retardation, we imaged a tissue-like phantom consisting of a long birefringent band followed by four parallel elements with distinct birefringence levels and an optic axis orientation different from the long band (FIG. 8, panels (a) and (d)). FIG. 8, panels (b) and (e) present the cumulative retardation images from either side of the sample, corresponding to the retardation of P(x) reconstructed with conventional algorithms for single-input-state PS-OCT. FIG. 8, panels (c) and (f) show images of local retardation reconstructed using the polarization mirror state. Whereas cumulative retardation is difficult to interpret, the local retardation clearly reveals the individual sample segments with their distinct levels of birefringence and is recovered irrespective of the sample orientation.

FIG. 8, panels (g)-(j) demonstrate local retardation imaging of excised swine retina. The intensity image visualizes the layered structure of the retina (FIG. 8, panel (g)). The local retardation reveals the birefringence of the retinal nerve fiber layer (RNFL), clearly differentiating it from the less birefringent subsequent layers (FIG. 8, panel (h)). RNFL birefringence is being investigated for its potential in diagnosing early degeneration of the RNFL associated with glaucoma.

Previous strategies to reconstruct local birefringence from single-input-state PS-OCT rely on the intrinsic symmetry of the imaging system. Crucially, the evolution of v through the mirror state persists also in an imaging system with additional static, single-pass system components B and C in only the illumination or the detection paths, respectively, as frequently the case in fiber-based systems. They alter the observed polarization state to v(x)=C·P(x)·B·u. While P(x) is intrinsically D-transpose symmetric and hence a linear retarder, the presence of B and C modifies the overall transmission to become a general retarder. However, B·u merely defines a modified input state u'=B·u, which upon transmission through P(x) repeatedly evolves through the mirror state D·u'. The unitary matrix C simply rotates this polarization state evolution and maps the apparent mirror state to the observed mirror state C·D·B·u. With the presence of static, and possibly distinct, system components, the 'input' polarization state observed at the receiver in the absence of any sample transmission is C·B·u. The mirror state phenomenon ensures that the evolution of the polarization state including propagation through the sample P(x) evolves through the mirror state C·D·B·u=C·D·C$^T$·(C·B·u). Here C·D·C$^T$ defines a new symmetry plane, which is moved from the QU-plane defined by D under the similarity transformation by C. For reconstruction of the local retardation, only the mirror state, not the input state or symmetry plane, is required.

A remaining challenge manifests whenever v aligns with u', which impairs the reconstruction of local retardation and results in artificially high local retardation (white arrows in FIG. 8, panel (c)). Using circularly polarized input light requires a half wave of retardation to realize this alignment, which is uncommon in many biological samples. Yet, some tissues feature substantial birefringence and controlling the input state is not necessarily possible. The resulting artifacts can be avoided by introducing a modest amount of polarization mode dispersion (PMD) into the system and using spectral binning for reconstruction. As illustrated in FIG. 9, τ is reconstructed for each individual spectral bin, together with a reliability map expressing the alignment of v with u'. Because PMD disperses the input polarization state across the spectral bins, simultaneous alignment of v with u' in all bins is very unlikely. After aligning the rotation vectors between the spectral bins to compensate for PMD, they are weighted with the reliability metric and vectorially averaged (see below for further information). The norm of the averaged τ finally provides the local sample retardation, free from artifacts, as demonstrated in FIG. 9, panel (i) for a tissue-like phantom.

FIG. 9 shows a demonstration of application of the mirror state constraint in a fiber-based system and removal of the alignment-induced error by using the wavelength-dependence of the polarization states with spectral binning. Panel (a) shows a simplified schematic of the sample arm of a fiber-based interferometric imaging system. L1-L2, lenses, PC, polarization controller, M, scanning mirror, SMF, single mode fiber. Panel (b) shows the principle of spectral binning, in which the full spectrum is divided into 9 bins by multiplication with 9 Hanning windows. Panel (c) shows an illumination state of polarization (SOP) of each spectral bin. The variation of SOPs is caused by PMD induced by the polarization controller. Panels (d)-(i) show cross-sectional images of two-layer phantom reconstructed with different spectral bins. Panel (d) shows local retardation resolved using the 1st spectral bin. Panel (e) shows local retardation resolved using the 9th spectral bin. Panel (f) shows the reliability metric map of 1st spectral bin. Panel (g) shows the reliability metric map of 9th spectral bin. Panel (h) shows a cross-sectional birefringence image reconstructed using the whole spectrum. Panel (i) shows a cross-sectional birefringence image reconstructed with spectral binning method. Scale bars in panel (i) for panels (d)-(i), vertical: 100 μm, horizontal: 400 μm.

Thus, demonstrated herein are apparatus, methods, and systems for obtaining polarization information from a sample based on the peculiar properties of the mirror polarization state when measuring backscattered light along identical illumination and detection paths free of polarization-dependent loss. In PS-OCT, the mirror state constrains the evolution of the depth-dependent polarization state and enables local retardation imaging, which previously has not been available to PS-OCT without substantially more complex measurements using multiple input states.

Experimental Setup

A single-input-state polarization-sensitive spectral domain optical coherence tomography (PS-SD-OCT) system was used for certain embodiments disclosed herein. The unpolarized light from a supercontinuum source was linearly polarized, adjusted with an achromatic quarter-wave-plate to circular polarization, unless otherwise noted, and split by a free-space beam splitter into reference and sample arms. A linear polarizer oriented at 45° in the reference arm defined the reference polarization state independent of the source polarization. In each of the interferometer arms, by means of a flip-mirror, the light was directed either in free space to the sample and the reference mirror, respectively, or first coupled through 1.5 m of single mode fiber. A three-paddle polarization controller was applied in each fiber for polarization management. For sample imaging, the light was focused with a 30 mm focal length lens, achieving a FWHM spot diameter of ~8 and scanned with a galvanometric mirror in both lateral directions. At the exit port of the beam splitter, a half-wave plate allowed precisely aligning the polarization axes of the sample and reference light with the slow and fast axis of a polarization maintaining (PM) fiber. The polarization states of the PM fiber were subsequently split with a polarizing beam splitter towards two identical custom-built spectrometers to record the interference pattern of the horizontal (h) and vertical (v) polarization components, respectively. The detected source bandwidth was about 160 nm centered on 840 nm, providing a measured axial resolution of ~2.5 μm in air. Recorded spectra were pre-processed by background-subtraction, alignment between the two spectrometers, interpolation to linear wavenumber k, and compensation for dispersion imbalance between the sample and reference arms. Further details of the optical system are provided below.

Data Processing

For the initial demonstration of the polarization mirror state, light was directed through the fibers and reflected off a mirror in the sample arm. The paddles of the polarization controller in the sample arm were dynamically moved while recording interference signals. The analytic signal of the pre-processed interference patterns $f_{h,v}(k)$ was constructed by setting the negative delays to zero: $f_{h,v}(k) = FT^{-1}\{FT\{f_{h,v}(k)\} \cdot H(z)\}$ where $H(z)$ is the Heaviside step-function, FT is the Fourier transform, and z is the Fourier transform variable, corresponding to the optical path length difference. We then computed the Stokes parameters $[I\ Q\ U\ V]^T = [|f_h|^2 + |f_v|^2 \quad |f_h|^2 - |f_v|^2\ 2\mathrm{Re}\{f_h f_v^*\}\ -2\mathrm{Im}\{f_h f_v^*\}]^T$, where * indicates complex conjugation. We averaged the Stokes vectors around the central wavenumber $k_c$ with a Gaussian kernel of ⅕th of the full recorded spectral width and computed the normalized three-component Stokes vector $s = [Q\ U\ V]^T/(Q^2 + U^2 + V^2)^{1/2}$. The measurements are comparable to using a conventional polarimeter in combination with a monochromatic laser source. The input polarization state was determined without the fiber segments in the two arms.

For the evolution of the polarization states within the three-layer phantom, the pre-processed spectral fringe data was Fourier-transformed to obtain tomograms $t_{h,v}(z) = FT\{f_{h,v}(k)\}$, cast into Stokes parameters as described above, spatially filtered with a two-dimensional Gaussian kernel of width 20 μm in the axial direction and 80 μm in the lateral direction, and normalized to obtain the three-component Stokes vector s(z). For processing the retinal data, filtering was also performed in the second lateral direction, using the same kernel.

For reconstruction of local retardation, we employed the pre-calibrated polarization mirror state u' and implemented Eq. (4) by approximating $v = (s[n+1] + s[n])/2$ and $\delta v/\delta x = (s[n+1] - s[n])/\Delta z$, where n is the pixel index along depth $z = n\Delta z$, and $\Delta z$ is the axial sampling distance. To avoid high-frequency noise introduced by taking the difference between adjacent points, we axially averaged the reconstructed rotation vector t(z) with a rectangular Gaussian window of length 20 pixels, before computing its norm as the local retardation image, scaled to degrees of retardation per depth (°/μm). For comparison, cumulative retardation was computed by evaluating the angle between s(z) at each depth and $s(z_{surf})$, where $z_{surf}$ is the axial location of the sample surface within each depth profile.

For suppression of the artifacts when the mirror state aligns with the apparent optic axis, we multiplied the pre-processed spectra with Hanning windows han(k, m) of width $\Delta k/N$ centered on $m\Delta k/(2N)$ within the available k-support, $\Delta k$, $m \in [1, 2N-1]$, $N=5$, resulting in 9 spectral bins, to compute the binned Stokes vectors s(z,m). We also evaluated the degree of polarization $DOP = \langle (Q^2 + U^2 + V^2)^{1/2}/I \rangle$, where $\langle\ \rangle$ indicates averaging over the spectral bins, and Q, U, V and I are the spatially filtered Stokes components before normalization, to later serve as a metric to identify meaningful polarization signals. Following the identical processing for local retardation as described above for each bin, we obtained the rotation vectors t(z,m). They all describe the same sample birefringence, but may be offset in their relative orientation due to system PMD, introduced by the polarization controller paddles in the sample arm fiber. The required rotation R(m) to align the vectors of each bin to the central bin N in the least-square sense is given by:

$$\max_{R(m)} Tr\left(R(m) \cdot \sum_{B-scan} \tau(x, z, m) \cdot \tau^T(x, z, N) \cdot w(x, z)\right), \quad (5)$$

where $w(x,z) = 1 - v^T \cdot u'$ is a weight expressing the reliability of the given Stokes vector by its projected distance from the mirror state, R(m) is assumed constant within an entire B-scan, and the sum is taken over all points with sufficient DOP>0.8 and signal intensity SNR>5 dB. From the singular value decomposition of the 3×3 matrix defined by the summation $\Sigma \tau \cdot \tau^T \cdot w = U \cdot D \cdot V^\dagger$, the solution to Eq. (5) is obtained by $R = V \cdot UV^\dagger$. Lastly, the aligned rotation vectors are averaged among the spectral bins considering their weights w(x,z), and then axially filtered, as previously, to obtain the final local retardation image.

Birefringence Phantom

We cut bands from scattering films of acrylonitrile butadiene styrene (ABS) and stretched them after heating above their glass-transition temperature. The three-layer phantom assembled three birefringent bands oriented at around 30° and 60° with respect to the first layer. The second sample consists of one long band above four short segments with distinct birefringence. The angle between the stretching directions of bands in the first layer and second layer is ~45°. Bands were embedded in ultrasound gel mixed with polystyrene beads (Polysciences Inc., 300 nm in diameter) to provide a non-birefringent scattering matrix.

Retinal Imaging

Swine eyes were collected from a butcher and imaging was carried out within two hours after the eyeball was harvested. We cut the eyeball along the equator, removed the lens, emptied the vitreous chamber, and instilled just enough normal saline to prevent specular reflection while scanning the retina. The scanning area centered on the optical nerve head.

Muller Matrix of Reverse Transmission Through a Reciprocal Medium

In this section, we derive the deterministic (i.e. non-depolarizing) Muller matrix of the reverse transmission through a reciprocal element from its corresponding Jones expression. If A and B denote the front and rear interface of this element, the Jones matrix $J_{AB}$ describes the forward propagation through this element (as shown in FIG. 10). The reverse transmission is given by the transpose of this matrix $J_{BA} = J^T_{AB}$, when maintaining the orientation of the spatial xy-coordinates irrespective of the propagation direction.

A matrix J in the Jones formalism can be converted into its corresponding Mueller matrix M using:

$$M = U(J \otimes \bar{J})U^\dagger \quad (6)$$

$$U = \frac{1}{\sqrt{2}}\begin{bmatrix} 1 & 0 & 0 & 1 \\ 1 & 0 & 0 & -1 \\ 0 & 1 & 1 & 0 \\ 0 & i & -i & 0 \end{bmatrix},$$

where $\otimes$ is the Kronecker tensor product, $\bar{J}$ is the complex conjugate of J, and $U^\dagger$ represents the conjugate transpose of U, corresponding also to its inverse. Using the fact that the transpose is distributive for the Kronecker product $((A \otimes B)^T = A^T \otimes B^T)$, we find $$\begin{aligned}
M_{RA} &= U \cdot (J_{RA} \otimes \overline{J_{RA}}) \cdot U^\dagger \quad (7) \\
&= U \cdot (J_{AB}^T \otimes \overline{J_{AB}^T}) \cdot U^\dagger \\
&= U \cdot (J_{AB}^T \otimes \overline{J_{AB}})^T \cdot U^\dagger \\
&= U \cdot I \cdot (J_{AB} \otimes \overline{J_{AB}})^T \cdot I \cdot U^\dagger \\
&= U \cdot (U^T \cdot \overline{U}) \cdot (J_{AB} \otimes \overline{J_{AB}})^T \cdot (U^T \cdot \overline{U}) \cdot U^\dagger \\
&= (U \cdot U^T) \cdot \overline{U} \cdot (J_{AB} \otimes \overline{J_{AB}})^T \cdot U^T \cdot (\overline{U} \cdot U^\dagger) \\
&= (U \cdot U^T) \cdot M_{AB}^T \cdot (\overline{U} \cdot U^\dagger)
\end{aligned}$$

Evaluating the outermost expressions, we find $U \cdot U^T = U \cdot U^\dagger = \mathrm{diag}(1,1,1,-1)$. The transpose of a Jones matrix corresponds to the transpose of its corresponding Mueller matrix, with the sign of the last row and column, excluding the on-diagonal element, inverted. It represents the reverse transmission through a reciprocal element. For a pure retardation matrix R in the SO(3) formalism, this results in $R_{BA} = D \cdot R^T_{AB} \cdot D$, where $D = \mathrm{diag}(1,1,-1)$.

Determination of Rotation Vector

The effect of a linear retarder can be expressed as a rotation vector $\omega = \varphi \cdot p = \varphi \cdot [\cos \alpha, \sin \alpha, 0]^T$, where p has unitary length, $\alpha$ is the azimuth angle with respect to the Q-axis and $\varphi$ is the rotation angle. The corresponding SO(3) rotation matrix is:

$$P = I + \sin\varphi K + (1 - \cos\varphi)K^2 = \exp(\varphi K) \quad (8)$$

$$K = \begin{bmatrix} 0 & p_3 & -p_2 \\ -p_3 & 0 & p_1 \\ p_2 & -p_1 & 0 \end{bmatrix} = \begin{bmatrix} 0 & 0 & -\sin\alpha \\ 0 & 0 & \cos\alpha \\ \sin\alpha & -\cos\alpha & 0 \end{bmatrix}.$$

Here, we are looking for the linear retarder $P(\varphi, \alpha)$ that maps an input state $u = [u_1, u_2, u_3]^T$ to some state $v = [v_1, v_2, v_3]^T$. Its rotation axis is given by the intersection of the QU-plane and the plane bisecting u and v:

$$(v - u) \times \begin{bmatrix} 0 \\ 0 \\ 1 \end{bmatrix} = \begin{bmatrix} v_2 - u_2 \\ u_1 - v_1 \\ 0 \end{bmatrix}, \quad (9)$$

from where $$\alpha = \tan^{-1}\left(\frac{u_1 - v_1}{v_2 - u_2}\right). \quad (10)$$

In general, u and v clearly define a single rotation axis. Only for the mirror polarization state, in which case both the nominator and denominator vanish, $\alpha$ is undefined and can take any value. To find the amount of rotation around this axis required to map u onto v, we project both vectors onto the plane orthogonal to the rotation axis and evaluate their relative angle:

$$\begin{aligned}
\varphi &= \cos^{-1}\left(\frac{(u - (p^T \cdot u)p)^T \cdot (v - (p^T \cdot v)p)}{\sqrt{1 - (p^T \cdot u)^2}\sqrt{1 - (p^T \cdot v)^2}}\right) \\
&= \cos^{-1}\left(\frac{u^T \cdot v - (p^T \cdot u)^2}{1 - (p^T \cdot u)^2}\right)
\end{aligned} \quad (11)$$

where $p = [\cos \alpha, \sin \alpha, 0]^T$, and $p^T \cdot u = p^T \cdot v$ by construction. A defined rotation vector $\omega$ within the QU-plane maps u onto a general v. Only for the mirror state $v = u'$, there exists a rotation for any azimuth direction within the QU-plane, tracing out a continuous curve in the QU-plane when wrapped to $\varphi \in (-\pi, \pi)$ (the red curve in FIG. 11, panel (b)).

The shape and orientation of this trace is determined by u. Assuming the azimuth and elevation angles of u are $\eta$ and $\varepsilon$, respectively $$\left(\eta \in [0, 2\pi), \varepsilon \in \left[-\frac{\pi}{2}, \frac{\pi}{2}\right]\right),$$

then the largest rotation angle $\varphi = \pi$ appears when the rotation vector aligns with the projection of u onto the QU-plane, indicated by $\tau_{An}$ in FIG. 11, panel (a). The smallest rotation angle appears when the rotation axis $\tau_{Bn}$ is perpendicular to $\tau_{An}$. In this case the rotation trajectory coincides with a longitude of the sphere and corresponds to a rotation angle of $\omega_B = 2|\varepsilon|$ ($\varepsilon$ is the elevation angle of u). As visualized in FIG. 11, panel (b), the long axis of the trace aligns with the azimuth angle of input state u, and its curvature is determined by the elevation angle of u.

Polarization State Evolution Through the Mirror State

According to Eq. 2 the evolution of the polarization state v is determined by $\tau \times$. Replacing P with the expression in Eq. 1, we obtain $$\tau x = D \cdot A^T \cdot M^T \cdot D \cdot \underbrace{\left(D \cdot M \cdot \frac{\partial M^T}{\partial x} \cdot D + \frac{\partial M}{\partial x} \cdot M^T\right)}_{qx} \cdot D \cdot M \cdot A \cdot D = \quad (12)$$

$$D \cdot A^T \cdot M^T \cdot D \cdot qx \cdot D \cdot M \cdot A \cdot D.$$

$qx$ is not only skew-symmetric, but also D-transpose symmetric, confining q to the QU-plane. However, the similarity transformation of $qx$ by $D \cdot A^T \cdot M^T \cdot D$ rotates the apparent optic axis q out of the QU-plane, in general. Re-integrating $\partial v / \partial x$ of Eq. 2 at a given x we obtain the first-order approximation to the evolution of v:

$$v'(x + \Delta x) = \exp(\Delta x \cdot \tau \times) \cdot v(x) = D \cdot A^T \cdot M^T \cdot D \cdot \exp(\Delta x \cdot q \times) \cdot M \cdot A \cdot u. \quad (13)$$

Here, we used v=D·A$^T$·M$^T$·D·M·A·u and the property of the matrix exponential exp(A·B·A$^{-1}$)=A·exp(B)·A$^{-1}$. Δx determines the amount of retardance of the linear retarder exp (Δx·q×). As explained above, it is always possible to find the suitable retardance for the given orientation of q within the QU-plane to map M·A·u onto its mirror state D·M·A·u, which leads to v=D·u. Hence, the first order approximation of the polarization state evolution at a given depth lies on a circle evolving (periodically) through the mirror state. Because q× is constant within a homogeneously birefringent sample layer the first order evolution is independent of depth within this layer, and the polarization state follows closely the approximated circle. Of note, the apparent rotation axis T is related to the true sample optic axis q× through a similarity transform with D·A$^T$·M$^T$·D.

FIG. 12 shows a setup that may be used in various embodiments disclosed herein. SCL: Supercontinuum laser, L1-L15: Lenses, P1-P2: Polarizers, Q1: Quarter wave plate, H1: Half wave plate, BS: Beam splitter, PBS: Polarizing beam splitter, SP: Spectrometers, M1-M5: Mirrors, FM1-FM2: Flip mirrors, PC1-PC2: Polarization controllers, SMF: single mode fiber, PMF: polarization maintaining fiber, DC: Dispersion compensation. SCL: supercontinuum laser, DK-3460, NKT Photonics Inc. P1,P2: Polarizer, LPNIRE100-B, Thorlabs Inc. Q1: Quarter-wave plate, AQWP10M-980, Thorlabs Inc. H1: Half-wave plate AHWP10M-980, Thorlabs Inc. BS: Non-polarizing beam splitter (50/50), BS014, Thorlabs Inc. PBS: Polarizing beam splitter (50/50), PBS202, Thorlabs Inc. DC: Dispersion compensation, BK7 glass plate. SP: Spectrometer. Each custom spectrometer consisted of transmission grating (Wasatch TG: 1200 line/mm), camera lens (L9: Nikon AF 85 mm f/1.8D) and line scan CCD (E2V AVIIVA EV71YEM4CL2010-BA9). SMF: Single-mode fiber, 780HP, Thorlabs Inc. PMF: polarization maintaining fiber, P3-780PM-FC-2, Thorlabs Inc. PC: Polarization controller. Three-paddle polarization controllers, with 1, 2 and 1 fiber loops in the three paddles, respectively.

Turning to FIG. 13, an example 1300 of a system for determining a retardance of a layer of a sample is shown in accordance with some embodiments of the disclosed subject matter. As shown in FIG. 13, a computing device 1310 can receive polarization data from a detector 1302 such as a detector associated with a PS-OCT system. In some embodiments, computing device 1310 can execute at least a portion of a retardance determination system 1304 to determine retardance of a layer of a sample based on the polarization data received from the detector 1302. Additionally or alternatively, in some embodiments, computing device 1310 can communicate information about the polarization data received from the detector 1302 to a server 1320 over a communication network 1306, which can execute at least a portion of retardance determination system 1304 to determine retardance of a layer of a sample based on the polarization data received from the detector 1302. In some such embodiments, server 1320 can return information to computing device 1310 (and/or any other suitable computing device) indicative of an output of retardance determination system 1304. This information may be transmitted and/or presented to a user (e.g. an operator, a clinician, etc.) and/or may be stored (e.g. as part of a medical record associated with the subject).

In some embodiments, computing device 1310 and/or server 1320 can be any suitable computing device or combination of devices, such as a desktop computer, a laptop computer, a smartphone, a tablet computer, a wearable computer, a server computer, a virtual machine being executed by a physical computing device, etc.

In some embodiments, detector 1302 can be any suitable detector for use with performing polarization-sensitive optical coherence tomography (PS-OCT). In some embodiments, interferometric detector 1302 can be local to computing device 1310. For example, detector 1302 may be incorporated with computing device 1310 (e.g., computing device 1310 can be configured as part of a device for detecting light as part of a PS-OCT system). As another example, detector 1302 may be connected to computing device 1310 by a cable, a direct wireless link, etc. Additionally or alternatively, in some embodiments, detector 1302 can be located locally and/or remotely from computing device 1310, and can communicate polarization information to computing device 1310 (and/or server 1320) via a communication network (e.g., communication network 1306).

In some embodiments, communication network 1306 can be any suitable communication network or combination of communication networks. For example, communication network 1306 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, WiMAX, etc.), a wired network, etc. In some embodiments, communication network 1306 can be a local area network, a wide area network, a public network (e.g., the Internet), a private or semi-private network (e.g., a corporate or university intranet), any other suitable type of network, or any suitable combination of networks. Communications links shown in FIG. 13 can each be any suitable communications link or combination of communications links, such as wired links, fiber optic links, Wi-Fi links, Bluetooth links, cellular links, etc.

FIG. 14 shows an example 1400 of hardware that can be used to implement computing device 1310 and server 1320 in accordance with some embodiments of the disclosed subject matter. As shown in FIG. 14, in some embodiments, computing device 1310 can include a processor 1402, a display 1404, one or more inputs 1406, one or more communication systems 1408, and/or memory 1410. In some embodiments, processor 1402 can be any suitable hardware processor or combination of processors, such as a central processing unit, a graphics processing unit, etc. In some embodiments, display 1404 can include any suitable display devices, such as a computer monitor, a touchscreen, a television, etc. In some embodiments, inputs 1406 can include any suitable input devices and/or sensors that can be used to receive user input, such as a keyboard, a mouse, a touchscreen, a microphone, etc.

In some embodiments, communications systems 1408 can include any suitable hardware, firmware, and/or software for communicating information over communication network 1306 and/or any other suitable communication networks. For example, communications systems 1408 can include one or more transceivers, one or more communication chips and/or chip sets, etc. In a more particular example, communications systems 1408 can include hardware, firmware and/or software that can be used to establish a Wi-Fi connection, a Bluetooth connection, a cellular connection, an Ethernet connection, etc.

In some embodiments, memory 1410 can include any suitable storage device or devices that can be used to store instructions, values, etc., that can be used, for example, by processor 1402 to present content using display 1404, to communicate with server 1320 via communications system(s) 1408, etc. Memory 1410 can include any suitable volatile memory, non-volatile memory, storage, or any suitable combination thereof. For example, memory 1410 can include RAM, ROM, EEPROM, one or more flash drives, one or more hard disks, one or more solid state drives, one or more optical drives, etc. In some embodiments, memory 1410 can have encoded thereon a computer program for controlling operation of computing device 1310. In such embodiments, processor 1402 can execute at least a portion of the computer program to present content (e.g., images, user interfaces, graphics, tables, etc.), receive content from server 1320, transmit information to server 1320, etc.

In some embodiments, server 1320 can include a processor 1412, a display 1414, one or more inputs 1416, one or more communications systems 1418, and/or memory 1420. In some embodiments, processor 1412 can be any suitable hardware processor or combination of processors, such as a central processing unit, a graphics processing unit, etc. In some embodiments, display 1414 can include any suitable display devices, such as a computer monitor, a touchscreen, a television, etc. In some embodiments, inputs 1416 can include any suitable input devices and/or sensors that can be used to receive user input, such as a keyboard, a mouse, a touchscreen, a microphone, etc.

In some embodiments, communications systems 1418 can include any suitable hardware, firmware, and/or software for communicating information over communication network 1306 and/or any other suitable communication networks. For example, communications systems 1418 can include one or more transceivers, one or more communication chips and/or chip sets, etc. In a more particular example, communications systems 1418 can include hardware, firmware and/or software that can be used to establish a Wi-Fi connection, a Bluetooth connection, a cellular connection, an Ethernet connection, etc.

In some embodiments, memory 1420 can include any suitable storage device or devices that can be used to store instructions, values, etc., that can be used, for example, by processor 1412 to present content using display 1414, to communicate with one or more computing devices 1310, etc. Memory 1420 can include any suitable volatile memory, non-volatile memory, storage, or any suitable combination thereof. For example, memory 1420 can include RAM, ROM, EEPROM, one or more flash drives, one or more hard disks, one or more solid state drives, one or more optical drives, etc. In some embodiments, memory 1420 can have encoded thereon a server program for controlling operation of server 1320. In such embodiments, processor 1412 can execute at least a portion of the server program to transmit information and/or content (e.g., results of a tissue identification and/or classification, a user interface, etc.) to one or more computing devices 1310, receive information and/or content from one or more computing devices 1310, receive instructions from one or more devices (e.g., a personal computer, a laptop computer, a tablet computer, a smartphone, etc.), etc.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

FIG. 15 shows an example 1500 of a process for determining a retardance of a layer of a sample in accordance with some embodiments of the disclosed subject matter. As shown in FIG. 15, at 1502, process 1500 can transmit a first portion of a polarized light to a sample arm of an optical system and a second portion of the polarized light to a reference arm of the optical system. At 1504, process 1500 can combine first return light returned from the sample arm and second return light from the reference arm. At 1506, process 1500 can detect the combined light along a first polarization state and a second polarization state to produce polarization data, where the second polarization state may be different from the first polarization state. At 1508, process 1500 can determine polarization states of light returning from upper and lower surfaces of a layer of the sample based on detecting the combined light. Finally, at 1510, process 1500 can determine a retardance of the layer of the sample based on the determined polarization states.

It should be understood that the above described steps of the processes of FIG. 15 can be executed or performed in any order or sequence not limited to the order and sequence shown and described in the figures. Also, some of the above steps of the processes of FIG. 15 can be executed or performed substantially simultaneously where appropriate or in parallel to reduce latency and processing times.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

What is claimed is:

1. A method for determining a retardance of a layer of a sample, comprising:
   transmitting a first portion of a polarized light to a sample arm of an optical system and a second portion of the polarized light to a reference arm of the optical system;
   combining first return light returned from the sample arm and second return light from the reference arm;
   detecting, using a detector, the combined light along a first polarization state and a second polarization state to produce polarization data,
   the second polarization state being different from the first polarization state;
   determining, using a processor coupled to the detector, polarization states of light returning from upper and lower surfaces of a layer of the sample based on detecting the combined light;
   determining, using the processor, a retardance of the layer of the sample based on the determined polarization states; and
   determining, using the processor, a mirror state associated with the polarization data.

2. The method of claim 1, wherein the mirror state comprises a point on a Poincaré sphere.

3. The method of claim 1, wherein the mirror state comprises an input polarization state with reversed helicity.

4. The method of claim 1, wherein the layer of the sample comprises a subsurface layer of the sample.

5. The method of claim 1, wherein the optical system comprises an optical coherence tomography system, and
wherein detecting the combined light along a first polarization state and a second polarization state further comprises:
detecting the combined light along a first polarization state and a second polarization state using the optical coherence tomography system.

6. The method of claim 1, wherein determining polarization states of light returning from upper and lower surfaces of a layer of the sample further comprises:
determining a rotation angle and a rotation axis of a rotation circle associated with the polarization states from upper and lower surfaces of the layer of the sample, and
determining a retardance level and an apparent optic axis based on determining the rotation angle and the rotation axis, respectively.

7. The method of claim 1, wherein the sample comprises a plurality of layers, and
wherein determining a retardance of a layer of the sample based on the determined polarization states further comprises:
determining a retardance of each of the plurality of layers of the sample based on the determined polarization states, and
wherein the method further comprises:
generating a reconstruction of the sample based on the retardance of each of the plurality of layers of the sample.

8. The method of claim 1, wherein determining a retardance of a layer of the sample further comprises:
determining the retardance of the layer of the sample using the wavelength-dependence of the polarization states to reduce artifacts.

9. The method of claim 8, wherein determining the retardance of the layer of the sample using the wavelength-dependence of the polarization states to reduce artifacts further comprises:
determining the retardance of the layer of the sample using the wavelength-dependence of the polarization states to reduce artifacts based on spectral binning.

10. The method of claim 1, wherein the polarized light comprises circularly polarized light.

11. The method of claim 1, wherein the detector comprises a first detector and a second detector, and
wherein detecting the combined light along a first polarization state and a second polarization state to produce polarization data further comprises:
transmitting the combined light to a polarizing beam splitter,
wherein the polarizing beam splitter transmits light having the first polarization state to the first detector and light having the second polarization state to the second detector.

12. The method of claim 1, wherein the sample comprises at least one of an ophthalmologic sample, a dermatological sample, an intravascular sample, or a gastrointestinal sample.

13. The method of claim 1, wherein the optical system comprises a polarization sensitive optical coherence tomography (PS-OCT) system.

14. An apparatus for determining a retardance of a layer of a sample, comprising:
an interferometric optical system comprising a sample arm and a reference arm;
a light source coupled to the optical system,
the light source is configured for providing a first portion of a polarized light to the sample arm and a second portion of the polarized light to the reference arm, and
the optical system is configured for combining first return light returned from the sample arm and second return light from the reference arm;
a detector to detect the combined light along a first polarization state and a second polarization state to produce polarization data,
the second polarization state being different from the first polarization state; and
a processor coupled to the detector, the processor is configured to:
determine polarization states of light returning from upper and lower surfaces of a layer of the sample based on the detector detecting the combined light,
determine a retardance of the layer of the sample based on the determined polarization states, and
determine a mirror state associated with the polarization data.

15. The apparatus of claim 14, wherein the mirror state comprises a point on a Poincaré sphere.

16. The apparatus of claim 14, wherein the mirror state comprises an input polarization state with reversed helicity.

17. The apparatus of claim 14, wherein the layer of the sample comprises a subsurface layer of the sample.

18. The apparatus of claim 14, wherein the optical system comprises an optical coherence tomography system, and
wherein the processor, when detecting the combined light along a first polarization state and a second polarization state, is further configured to:
detect the combined light along a first polarization state and a second polarization state using the optical coherence tomography system.

19. The apparatus of claim 14, wherein the processor, when determining polarization states of light returning from upper and lower surfaces of a layer of the sample, is further configured to:
determine a rotation angle and a rotation axis of a rotation circle associated with the polarization states from upper and lower surfaces of the layer of the sample, and
determine a retardance level and an apparent optic axis based on determining the rotation angle and the rotation axis, respectively.

20. The apparatus of claim 14, wherein the sample comprises a plurality of layers, and
wherein the processor, when determining a retardance of a layer of the sample based on the determined polarization states, is further configured to:
determine a retardance of each of the plurality of layers of the sample based on the determined polarization states, and
wherein the processor is further configured to:
generate a reconstruction of the sample based on the retardance of each of the plurality of layers of the sample.

21. The apparatus of claim 14, wherein the processor, when determining a retardance of a layer of the sample, is further configured to:

determine the retardance of the layer of the sample using the wavelength-dependence of the polarization states to reduce artifacts.

22. The apparatus of claim 21, wherein the processor, when determining the retardance of the layer of the sample using the wavelength-dependence of the polarization states to reduce artifacts, is further configured to:
   determine the retardance of the layer of the sample using the wavelength-dependence of the polarization states to reduce artifacts based on spectral binning.

23. The apparatus of claim 14, wherein the polarized light comprises circularly polarized light.

24. The apparatus of claim 14, wherein the detector comprises a first detector and a second detector, and
   wherein the apparatus is configured to transmit combined light to a polarizing beam splitter,
      wherein the polarizing beam splitter is configured to transmit light having the first polarization state to the first detector and light having the second polarization state to the second detector.

25. The apparatus of claim 14, wherein the sample comprises at least one of an ophthalmologic sample, a dermatological sample, an intravascular sample, or a gastrointestinal sample.

26. The apparatus of claim 14, wherein the optical system comprises a polarization sensitive optical coherence tomography (PS-OCT) system.

* * * * *

UNITED STATES PATENT AND TRADEMARK OFFICE
CERTIFICATE OF CORRECTION

| | | |
|---|---|---|
| PATENT NO. | : 11,473,897 B2 | Page 1 of 1 |
| APPLICATION NO. | : 17/284641 | |
| DATED | : October 18, 2022 | |
| INVENTOR(S) | : Brett Bouma et al. | |

It is certified that error appears in the above-identified patent and that said Letters Patent is hereby corrected as shown below:

In the Specification

Column 15, Line 5, "8 and" should be --~8 µm, and--.

Column 16, Line 33, "$R=V \cdot UV^{\dagger}$" should be --$R=V \cdot U^{\dagger}$--.

Signed and Sealed this
Tenth Day of January, 2023

Katherine Kelly Vidal
*Director of the United States Patent and Trademark Office*